(12) United States Patent
Dravid et al.

(10) Patent No.: US 9,095,629 B2
(45) Date of Patent: Aug. 4, 2015

(54) MAGNETIC NANOSTRUCTURES AS THERANOSTIC AGENTS

(75) Inventors: Vinayak P. Dravid, Glenview, IL (US); Saurabh Sharma, Arlington Heights, IL (US); Tadanori Tomita, Glenview, IL (US); Kirsten L. Viola, Lake Forest, IL (US); William L. Klein, Winnetka, IL (US)

(73) Assignees: NORTHWESTERN UNIVERSITY, Evanston, IL (US); ANN & ROBERT H. LURIE CHILDREN'S HOSPITAL OF CHICAGO, Chicago, IL (US)

( * ) Notice: Subject to any disclaimer, the term of this patent is extended or adjusted under 35 U.S.C. 154(b) by 379 days.

(21) Appl. No.: 13/505,167

(22) PCT Filed: Nov. 1, 2010

(86) PCT No.: PCT/US2010/054939
§ 371 (c)(1),
(2), (4) Date: Aug. 21, 2012

(87) PCT Pub. No.: WO2011/053901
PCT Pub. Date: May 5, 2011

(65) Prior Publication Data
US 2012/0308657 A1 Dec. 6, 2012

Related U.S. Application Data

(60) Provisional application No. 61/256,603, filed on Oct. 30, 2009.

(51) Int. Cl.
*H01F 1/00* (2006.01)
*A61K 41/00* (2006.01)
*A61K 49/18* (2006.01)
*A61K 47/48* (2006.01)
*B82Y 5/00* (2011.01)

(52) U.S. Cl.
CPC ....... *A61K 47/48623* (2013.01); *A61K 41/0052* (2013.01); *A61K 47/48861* (2013.01); *A61K 49/186* (2013.01); *A61K 49/1833* (2013.01); *A61K 49/1875* (2013.01); *B82Y 5/00* (2013.01)

(58) Field of Classification Search
CPC ............................ H01F 1/0054; A61K 49/186
USPC ........................................................ 424/429
See application file for complete search history.

(56) References Cited

U.S. PATENT DOCUMENTS

2006/0190063 A1  8/2006  Kanzius
2008/0187595 A1 * 8/2008  Jordan et al. .................. 424/490

OTHER PUBLICATIONS

Nayak et al. "Enhancing magnetic nanostructures for biomedicine", Nanoscape, 2007, vol. 4, Issue 1, pp. 73-79.*
Amstad et al., "Ultrastable iron oxide nanoparticle colloidal suspensions using dispersants with catechol-derived anchor groups." Nano Lett. Dec. 2009; 9(12):4042-8.
Gannon et al., "Intracellular gold nanoparticles enhance non-invasive radiofrequency thermal destruction of human gastrointestinal cancer cells." Journal of Nanobiotechnology 2008, 6:2.
Hilger, "Use of magnetic nanoparticle heating in the treatment of breast cancer." IEE Proc Nanobiotechnol. Feb. 2005; 152(1):33-9.
Ivkov et al., "Application of High Amplitude AlternatingMagnetic Fields for Heat Induction of Nanoparticles Localized in Cancer." Clin Cancer Res. Oct. 1, 2005;11(19 Pt 2):7093s-7103s.
Lambert et al., "accination with soluble Abeta oligomers generates toxicity-neutralizing antibodies." J Neurochem. Nov. 2001; 79(3):595-605.
Lambert et al., "Diffusible, nonfibrillar ligands derived from Abeta1-42 are potent central nervous system neurotoxins." Proc Natl Acad Sci U S A. May 26, 1998;95(11):6448-53.
Lambert et al., "Monoclonal antibodies that target pathological assemblies of Abeta." J Neurochem. Jan. 2007; 100 (1):23-35.
Moran et al., "Size-Dependent Joule Heating of Gold Nanoparticles Using Capacitively Coupled Radiofrequency Fields." Nano Res (2009) 2: 400-405.
Nayak et al., "Enhancing Magnetic Nanostructures for Biomedicine." Nanoscape 2007, 4(1):73-79.
Viola et al., "Why Alzheimer's is a disease of memory: the attack on synapses by a beta oligomers (ADDLs)." J Nutr Health Aging. Jan. 2008;12(1):51S-7S.

* cited by examiner

*Primary Examiner* — Gina Justice
(74) *Attorney, Agent, or Firm* — Tanya A. Arenson; Casimir Jones, S.C.

(57) ABSTRACT

The present invention relates to magnetic nanostructures as theranostic agents, which provide dual function as diagnostic and therapeutic agents. In particular, the present invention relates to compositions comprising magnetic nanostructures and their use as targeted therapeutic agents for cancers (e.g., medulloblastoma) and Alzheimer's disease and related diseases and conditions.

12 Claims, 36 Drawing Sheets

Figure 20

Qdot diffusion assays reveal ADDL scaffolding properties

| 15 seconds | 60 minutes |

Figure 22

Protection against ADDL synaptotoxicity by antisense-mGluR5 GNOs

Development of ScanImmuno Assay for ADDLs

Synthetic ADDL standard curve        Fractionated oligomers from AD brain

MAGNETIC NANOSTRUCTURES AS THERANOSTIC AGENTS

The present application is a national phase application under 35 U.S.C. §371 of PCT International Application No. PCT/US2010/054939, filed on Nov. 1, 2010, which claims priority to provisional application 61/256,603, filed Oct. 30, 2009, each of which are herein incorporated by reference in its entirety.

STATEMENT REGARDING FEDERALLY SPONSORED RESEARCH OR DEVELOPMENT

This invention was made with government support under Contract No. U54CA119341 awarded by the National Institutes of Health. The government has certain rights in the invention.

FIELD OF THE INVENTION

The present invention relates to magnetic nanostructures as theranostic agents, which provide dual function as diagnostic and therapeutic agents. In particular, the present invention relates to compositions comprising magnetic nanostructures and their use as targeted therapeutic agents for cancers (e.g., medulloblastoma) and Alzheimer's disease and related diseases and conditions.

BACKGROUND OF THE INVENTION

In the United States alone, new brain tumors develop in nearly 2,000 children and 35,000 adults each year. Most brain tumors are primary, meaning that they rarely spread beyond the brain, as opposed to metastatic. Brain tumors can be further divided into benign tumors which grow slowly and do not spread and malignant tumors that spread and invade surrounding tissues aggressively. More adults die each year of primary brain tumors than of Hodgkin's disease or multiple sclerosis, making it the third leading cause of death from cancers (Black, New Engl. J. Med. 1991, 324:1471-1476). Patients diagnosed with malignant gliomas have an average life expectancy of 36-48 weeks, and for the last several decades the survival rate has remained similar without dramatic improvement (Black, New Engl. J. Med. 1991, 324: 1471-1476).

Treatment of brain tumors faces a unique challenge compared to other types of cancers, due to the fact that not only are they developed within bone-covered structures (e.g., cranial cavity), thereby having restricted space to expand, but they are also embedded deeply within an organ carrying a multitude of vital functions. Therefore, even a benign tumor can be life-threatening if it is in an area of the brain that controls critical body functions such as breathing or blood circulation. Treatment normally begins with surgical resection and then follows with radiation or chemotherapy. Surgery faces the risk of removing surrounding tissues that may carry vital brain functions, while radiation and chemotherapy can both harm normal tissues that are near or along the treatment path. Indeed, if the tumor is in regions of cerebral hemispheres that control speech, vision, movement or cognition, surgery usually is not recommended. In addition, the use of radiation on children under the age of three is often prohibited because this is a critical time period of brain development. Chemotherapy, on the other hand, has been offering very limited applications, primarily attributed to the palliative response and limited duration of effects due to lack of targeting and selectivity of the drugs.

Primary brain tumors, including medulloblastoma, typically have poor prognosis in children, particularly if the primary tumor cannot be completely resected. Currently chemotherapy has done little to improve the outcomes for patient diagnosed with medulloblastoma. In addition, it recurs in a majority of patients and patients suffer significant morbidity related to current state-of-art therapeutic approaches. Hence, patients typically undergo multiple surgeries with reduced chances of survival.

Alzheimer's disease (AD) is the most common form of dementia. This incurable, degenerative, and terminal disease was first described by German psychiatrist and neuropathologist Alois Alzheimer in 1906 and was named after him. Generally, it is diagnosed in people over 65 years of age, although the less-prevalent early-onset Alzheimer's can occur much earlier. As of September 2009, this number is reported to be 35 million-plus worldwide.

AD develops for an indeterminate period of time before becoming fully apparent, and it can progress undiagnosed for years. The mean life expectancy following diagnosis is approximately seven years. Fewer than three percent of individuals live more than fourteen years after diagnosis.

Currently used treatments offer a small symptomatic benefit; no treatments to delay or halt the progression of the disease are as yet available. As of 2008, more than 500 clinical trials have been conducted for identification of a possible treatment for AD, but it is unknown if any of the tested intervention strategies will show promising results.

What is needed are additional methods of treating medulloblastoma and other cancers and central nervous system disorders such as Alzheimer's disease. Targeted treatment methods are particularly needed.

SUMMARY OF THE INVENTION

The present invention relates to magnetic nanostructures as theranostic agents, which provide dual function as diagnostic and therapeutic agents. In particular, the present invention relates to compositions comprising magnetic nanostructures and their use as targeted (e.g., localized) therapeutic agents for cancers (e.g., medulloblastoma) and Alzheimer's disease and related diseases and conditions.

Embodiments of the present invention provide systems of methods for diagnosing and treating any number of cancers and diseases (e.g., diseases spatially localized in or around tissue and organs). Embodiments of the present invention provide the advantage of allowing concurrent targeted diagnosis and treatment using the same magnetic nanostructures (e.g., by exposing the nanostructures to a radio frequency that generates heat following targeting).

For example, in some embodiments, the present invention provides a system, comprising a) a magnetic nanostructure (MNS) comprising i) a nanoparticle (e.g., coated with a non-magnetic coating) and ii) a targeting agent, wherein the targeting agent targets the nanostructure to a molecule of interest; and b) a device for generating a radio frequency, wherein the magnetic nanostructure generates heat when exposed to a radio frequency generated by the radio frequency generator. In some embodiments, the targeting agent is an antibody. In other embodiments, the molecule of interest is a cancer cell (e.g., a CNS cancer such as medulloblastoma). In some embodiments, the molecule of interest is an anti-Aβ-oligomer. In some embodiments, the system further comprises an imaging device (e.g., an MRI device). In some embodiments, the MNS are in a stable suspension. In some embodiments, nanoparticles are targeted via injection to the molecule of interest (e.g., at a disease site).

Embodiments of the present invention provide a method, comprising a) administering a magnetic nanostructure comprising i) a nanoparticle coated with a non-magnetic coating and ii) a targeting agent, wherein the targeting agent targets the nanostructure to a molecule of interest to a subject; b) detecting the presence of the molecule of interest in the subject by identifying the magnetic nanostructure; and c) destroying the molecule of interest by exposing the magnetic nanostructure to energy (e.g., radio frequency energy) that causes the magnetic nanostructure to destroy the molecule (e.g., via heating).

Additional embodiments provide a method, comprising a) administering a magnetic nanostructure comprising i) a nanoparticle coated with a non-magnetic coating and ii) a targeting agent, wherein the targeting agent targets the nanostructure to a molecule of interest to a subject; and b) detecting the presence of the molecule of interest in the subject by identifying the magnetic nanostructure. In some embodiments, identifying the magnetic nanostructure comprises the use of magnetic resonance imaging. In some embodiments, the method further comprising the step of destroying the molecule of interest by exposing the magnetic nanostructure to energy (e.g., radio frequency energy) that causes the magnetic nanostructure to destroy the molecule (e.g., via heating).

Further embodiments provide a method of treating cancer or Alzheimer's disease, comprising: a) administering a magnetic nanostructure comprising i) a nanoparticle coated with a non-magnetic coating and ii) a targeting agent, wherein the targeting agent targets the nanostructure to a molecule of interest (e.g., a cancer cell or an Alzheimer's disease specific molecule) to a subject; and b) contacting the nanostructure with energy (e.g., radio frequency energy) that causes the nanostructure to destroy or inactivate the molecule of interest (e.g., via heating). In some embodiment, MNS are locally delivered directly at a disease site or through a catheter or similar delivery vehicle for subsequent monitoring (e.g., diagnosis or monitoring of a therapy) and therapy.

Additional embodiments are described herein.

DESCRIPTION OF THE FIGURES

FIG. 20 shows Qdot diffusion assays for ADDL scaffolding properties.

FIG. 22 shows protection against ADDL synaptotoxicity by antisense-mGluR5 GNOs.

DEFINITIONS

Figure 1:
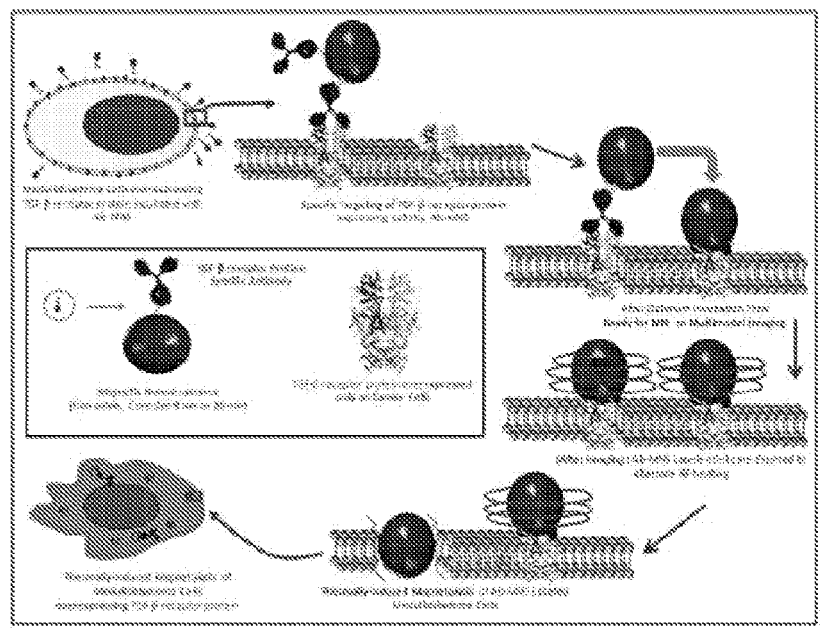
FIG. 1 shows an overview of theranostic management of medulloblastoma by Ab-MNS.
Figure 2:
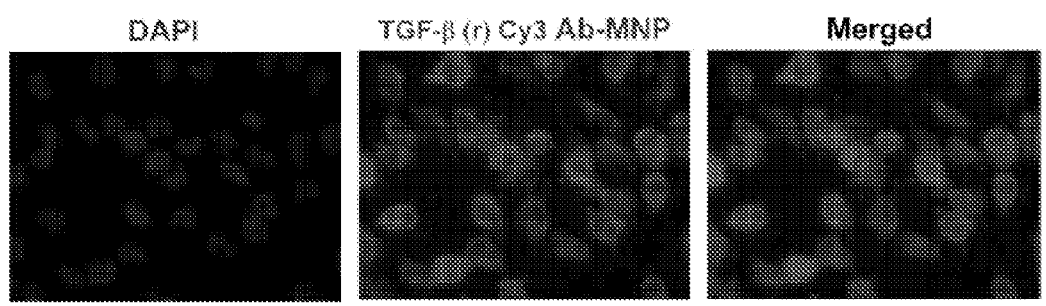
FIG. 2 shows fluorescent labeling of surface marker TGF-β by Ab-MNS.

As used herein, the term "agent" refers to a composition that possesses a biologically relevant activity or property. Biologically relevant activities are activities associated with biological reactions or events or that allows the detection, monitoring, or characterization of biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The agents of the present invention are not limited to these particular illustrative examples. Indeed any useful agent may be used including agents that deliver or destroy biological materials, cosmetic agents, and the like.

As used herein, the term "purified" or "to purify" refers to the removal of contaminants from a sample. For example, antibodies are purified by removal of contaminating non-immunoglobulin proteins; they are also purified by the removal of immunoglobulin that does not bind the target protein. The removal of non-immunoglobulin proteins and/or the removal of immunoglobulins that do not bind the target protein results in an increase in the percent of target reactive immunoglobulins in the sample.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to magnetic nanostructures as theranostic agents, which provide dual function as diagnostic (e.g., via imaging) and therapeutic (e.g., via heat inactivation) agents. In particular, the present invention relates to compositions comprising magnetic nanostructures and their use as targeted therapeutic agents for cancers (e.g., medulloblastoma) and Alzheimer's disease and related diseases and conditions.

Embodiments of the present invention disclose the synthesis of functionalized magnetic nanostructures that can selectively target molecular markers of cancers (e.g., CNS cancers such as medulloblastoma). These nanostructures are magnetically active and hence can be detected by conventional MRI. The agents serve as contrast agents and selective targeting agents. In some embodiments, when exposed to alternate magnetic fields, the nanostructures absorb radio frequency and generate heat that is sufficient to kill cells. Since these nanostructures are selectively bound to the tumor cells they only kill the tumor cell leaving healthy cells alone. A schematic of embodiments of the present invention is depicted in FIG. 1.

In some embodiments, magnetic nanostructures are encapsulated inside membranes or capsules of polymers or biomaterials which disrupt (or rupture) in response to local heating of magnetic nanostructures by RF field, thereby timing releasing of encased therapeutic or biochemical cargo at the local site.

Nanostructures with enhanced magnetic or optical properties have been increasingly warranted for their potential applications in upcoming "integrated diagnostic therapy". To meet this challenge embodiments of the present invention provide a wide range of magnetic nanostructure (MNS), "de novo theranostic agents", which provide high resolution, non-invasive multimodal imaging with improved sensitivity, specificity and cost effectiveness. At the same time, they respond to radio frequency energy (AC magnetic fields) and release heat as a result of rapid changes in magnetic orientation which induces apoptosis in cancer cells or degradation of selected proteins or otherwise kill or disable target cells. In some embodiments, these MNS exhibit enhanced T2 relaxation to darken the contrast media-containing structures.

Pathogenic events that initiate memory loss in AD are induced by the accumulation of potent neurotoxins. These neurotoxins arise from physiological proteins that mis-fold or mis-assemble, forming conformationally unique Ab species (Koo et al., (1999) Proc. Natl. Acad. Sci. U.S. A 96, 9989-9990; Selkoe, (2004) Nat. Cell Biol 6, 1054-1061; Walsh and Selkoe, (2004) Protein Pept. Lett. 11, 213-228). Early memory loss is considered the consequence of synapse failure, not neuron death, and is now widely attributed to pathogenic oligomers instead of the fibrillar Aβ of amyloid plaques (Hardy & Selkoe, (2002) Science 297, 353-356; Rodgers et al., (2005) Progress report on Alzheimer's disease 2004-2005. November 2005. U.S. Department of Health and Human Services; National Institutes on Aging; National Institutes of Health; Klein et al., (2001) Trends Neurosci. 24, 219-224; Selkoe, (2008) Behav. Brain Res. 192, 106-113; Glabe, (2008) J. Biol. Chem). The presence of a pathological species demonstrably absent from healthy individuals provides a target for immunotherapy. In some embodiments, elimination of these toxins stops disease progression and/or reverses the dysfunction in cognitive impairment and AD. Oligomers have been detected in vitro and in brain since the early 1990's but only after 1998 (Lambert et al, (1998) Proc. Natl. Acad. Sci. U.S.A 95, 6448-6453) have they been recognized as putative neurotoxins responsible for dementia. Oligomers are extracellular ligands (Gong et al., Proc. Natl. Acad. Sci. U.S.A 100, 10417-10422) that bind to specific synapses (Lacor et al., (2004) *J Neurosci.* 24, 10191-10200). They are markedly increased in human AD patients and show perineuronal localization in AD human brain tissue (Gong et al., supra; Lacor et al., supra; Chang et al., (2003) J. Mol. Neurosci. 20, 305-313; Lambert et al., (2009) CNS. Neurol. Disord. Drug Targets. 8, 65-81; Lambert et al., (2007) J Neurochem. 100, 23-35). To study these toxic Ab species, antibodies have been developed that prevent binding of aggregated Ab and the resulting responses in cultured cells.

The properties of Aβ oligomers and their role in Alzheimer's disease (AD) have become increasingly clear during the past decade (Viola et al, J Nutr Health 2008). Oligomers, unlike current drug targets, act as initiators of disease mechanisms and provide an optimal target for disease-modifying AD therapeutics. One approach with significant emerging interest is the use of nanotechnology for improved, more targeted, and less invasive diagnostics and therapeutics. An appealing feature of nanostructures with enhanced magnetic or optical properties is their application for integrated diagnostic therapy. Functional conjugates of highly specific anti-Aβ-oligomer (anti-ADDL) antibodies and magnetic nanostructures (Ab-MNS, core size 8 nm) were developed. Ab-MNS absorb radio frequency energy (AC magnetic fields) and release heat as a result of rapid changes in magnetic orientation which induces degradation of targeted proteins. These Ab-MNS also exhibit enhanced T2 relaxation to darken the contrast media-containing structures, offering a new resource for brain magnetic resonance imaging (MRI). In some embodiments, Ab-MNS (1) specifically target and isolate Aβ oligomers, (2) induce loss of oligomer toxicity through thermal activation induced by radio frequency, and (3) localize Aβ oligomers bound to neurons in vitro using MRI. Data presented here establish that these nanostructures find use in integrated diagnostic therapy for Alzheimer's disease. In general, molecular theranostic approaches promise high resolution, noninvasive multimodal imaging with improved sensitivity, specificity and cost effectiveness.

I. Nanoparticles

Embodiments of the present invention provide magnetic nanoparticles for use in research and clinical applications. In some embodiments, a single step process to synthesize robust magnetic nanostructures that are soluble and stable in aqueous solutions is utilized. MNS were characterized for their biocompatibility as well as magnetic and thermal properties. It was demonstrated that the optimum conditions for effective use of the functionalized MNS systems is a particle size between 8 and 20 nm to target, detect, image and denature single DAOY cell (Medulloblastoma cell line) or degrade ADDL protein molecules related to Alzheimer disease (AD), although certain indications may use other sizes and the invention is not limited to any particular size.

In some embodiments, MNS comprise a nanomaterial which includes a magnetic nanocomponent coated by a single or multiple layer(s) of non-toxic metal oxide(s), with or without inclusion of quantum dot materials; optionally comprising a bio-inert surface coating with or without addition of bioactive polymers or bio-molecules, depending on the different application purposes. In some embodiments, MNS further comprise a targeting agent (e.g., an antibody specific to the cell to be targeted).

In some embodiments, magnetic nanostructure are composed of aggregation or assembly at a coarser scale of smaller magnetic nanoparticles.

In some embodiments, the MNS comprise a magnetic core of $MnFe_2O_4$ or $NiFe_2O_4$. In some embodiments, the magnetic material is spherical, while in other embodiments it is irregular in shape (e.g., rods, needles or prisms). In some embodiments, the magnetic core is coated with a non magnetic shell for use in attaching targeting agents.

In some embodiments, the magnetic nanocomponent in the nanomaterial is a precursor for $\alpha\text{-}Fe_2O_3$, $\gamma\text{-}Fe_2O_3$ or related nanoalloy oxides with Fe after oxidization or for bcc-Fe or alloys-based Fe nanocomponents after reducing. The magnetic nanocomponent in the nanomaterials based on iron oxide can be extended to other iron oxide based nanomaterials, including, but not limited to, $MFe_2O_4$, $RFeO_3$, and $MRFeO_x$ (M=Ba, Bi, Co, Cr, Cu, Fe, Mg, Mn, Ni, Ti, Y, Zn) (R=rare earth metal elements) nanomaterials, and iron oxide coated various nanomaterials. In some embodiments, nanomaterials are $FeO_2$ nanoparticles.

The size of the completed nanomaterials in at least one dimension is preferably within 0.1-1000 nm, and even more preferably between 8 and 20 nm. The shape of the nanomaterials may be regular (column, cube, cylinder, pillar, pyramid, rod, sphere, tube etc.) or irregular/random. The shape of the nanomaterials is controlled by adjusting the reaction dynamics and aging/ripening time.

Magnetic nanoparticles used for biomedical applications generally comprise a composite where particles of a magnetic component are coated with a polymeric shell. The overall size of the composite, referred to as the hydrodynamic diameter, is different from the size of the core of magnetic crystals, which are mainly responsible for the magnetism of the composite. The magnetic core is made either by iron oxide compound comprising of a mixture of magnetite [Fe3O4] and maghemite [Fe2O3], or by transition metals such as Ni and Co. The polymeric shell often consists of a biocompatible polymer such as dextran or starch.

In some embodiments, magnetic nanoparticles are encapsulated inside liposomes, polymers, biopolymers or biomaterials along with therapeutic or biochemical cargo for controlled and timely release via rupturing of membrane by heat produced by magnetic nanostructure by external RF field.

In some embodiments, MNS are in a stable suspension. In some embodiments, stable suspensions are prepared as described in Example 7. Other methods are within the skill of one of ordinary skill in the art and may be utilized.

In some embodiments, a therapeutic agent (e.g., tumor or AD targeting agent) is associated with the MNS. The present invention is not limited to a particular drug. In some embodiments, the drug is a known chemotherapeutic agent (see below). In some embodiments, the chemotherapeutic agent is an agent known to be useful in treating cancer or Alzheimer's disease.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In some embodiments, anticancer agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) anti-androgens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |

TABLE 1-continued

| | | |
|---|---|---|
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequs Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |

TABLE 1-continued

| | | |
|---|---|---|
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$, Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14} \cdot (C_2H_4O_2)_x$] | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |

TABLE 1-continued

| | | |
|---|---|---|
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |

TABLE 1-continued

| | | |
|---|---|---|
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine (C$_{46}$H$_{56}$N$_4$O$_{10}$•H$_2$SO$_4$) | Velban | Eli Lilly |
| Vincristine (C$_{46}$H$_{56}$N$_4$O$_{10}$•H$_2$SO$_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

In some embodiments, the drug is an siRNA drug. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

II. Therapeutic Applications

As described above, embodiments of the present invention provide methods, systems and compositions for therapeutically targeting tumors (e.g., medulloblastoma) and structures associated with Alzheimer's disease, as well related diseases and conditions. Embodiments of the present invention provide methods and systems for using magnetic particles (MNS) comprising targeting moieties in therapeutic applications.

In some embodiments, the present invention provides compositions and methods for targeting brain and central nervous system tumors such as medulloblastoma. In some embodiments, MNS particles comprise targeting agents (e.g., antibodies specific for the cancer to be targeted).

In some embodiments, following targeting, MNS are heat activated in order to destroy cancerous tissue. In some embodiments, the size of MNS is optimized for heat therapy. For example, in some embodiments, smaller particles are optimal for heat inactivation. In some embodiments, a radio frequency (RF) field generated by an RF generator or a magnetic field generated by a magnetic field generator is utilized to provide heat for heat therapy of cancerous tissue.

In some embodiments, targeted MNS comprise anti-cancer therapeutics (e.g., those described above). The targeting agent is utilized to bring the therapeutic agent in close proximity to the cancerous tissue, thus protecting healthy tissue from damage. In some embodiments, targeting molecules include antibodies or receptors for tumor markers, e.g., CD 133 antibody for cancer tumors.

In some embodiments, MNS (e.g., uncoated MNS) are injected directly to the disease site for diagnostic and therapeutic applications.

Figure 3:
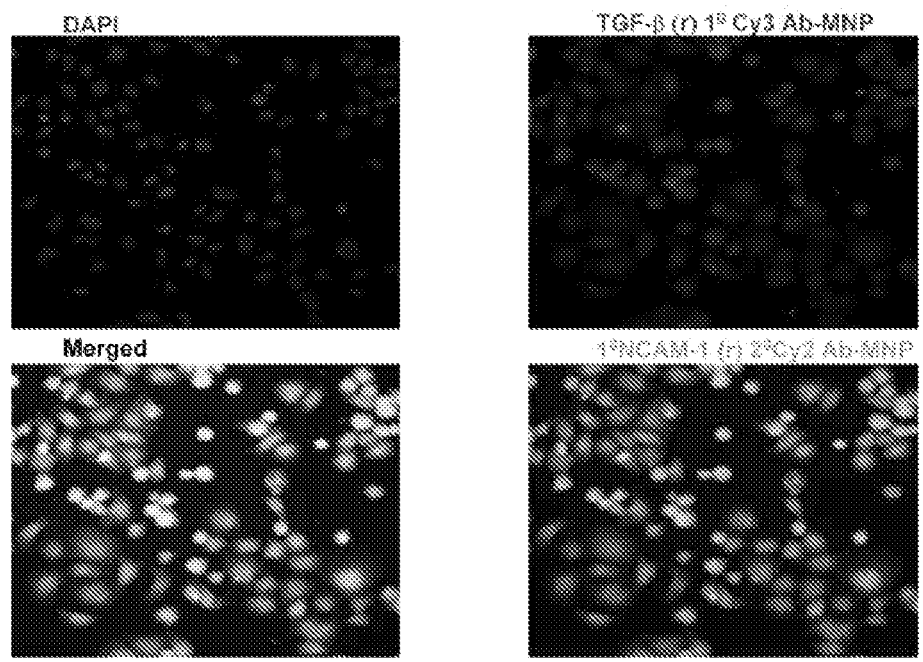
FIG. 3 shows co-targeting TGF-b (r) and NCAM-1 surface markers of medulloblastoma Cells by Antibody Functionalized MNS.
Figure 4:
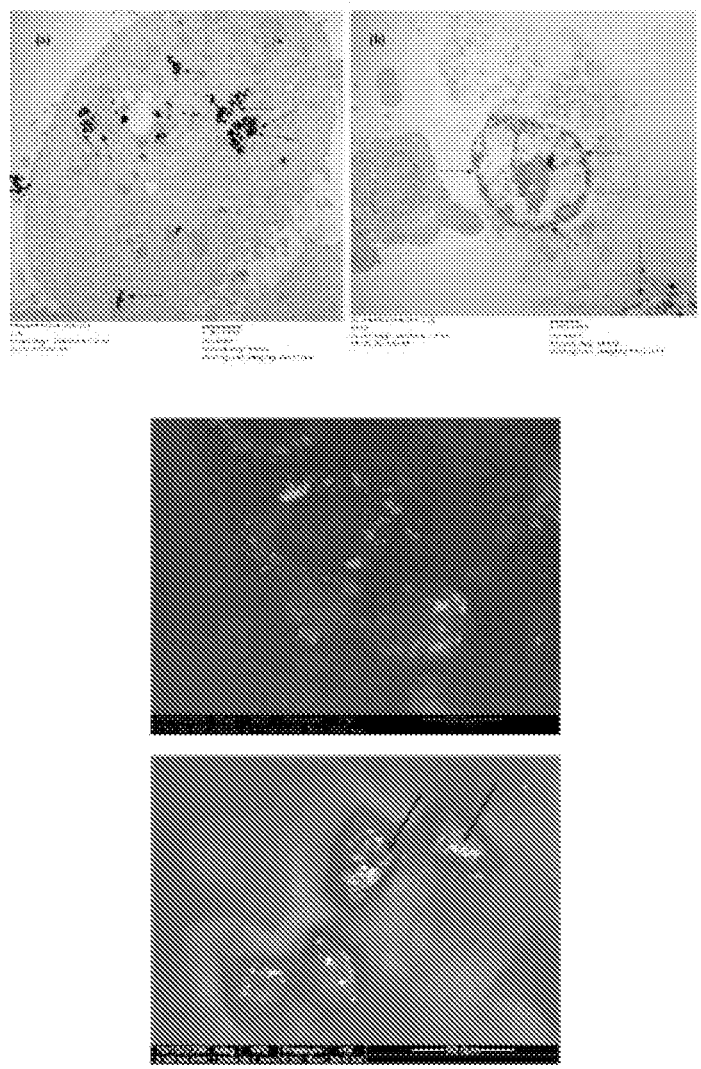
FIG. 4 shows a. TEM imaging of MNS internalized and Ab-MNs targeted cells. b. SEM imaging of MNS internalized and Ab-MNs targeted cells. c. AFM validation of surface targeting of medulloblastoma cells by Ab-MNS. d. Mapping of MRI images of FITC-MNP internalized medulloblastoma cells.
Figure 4:
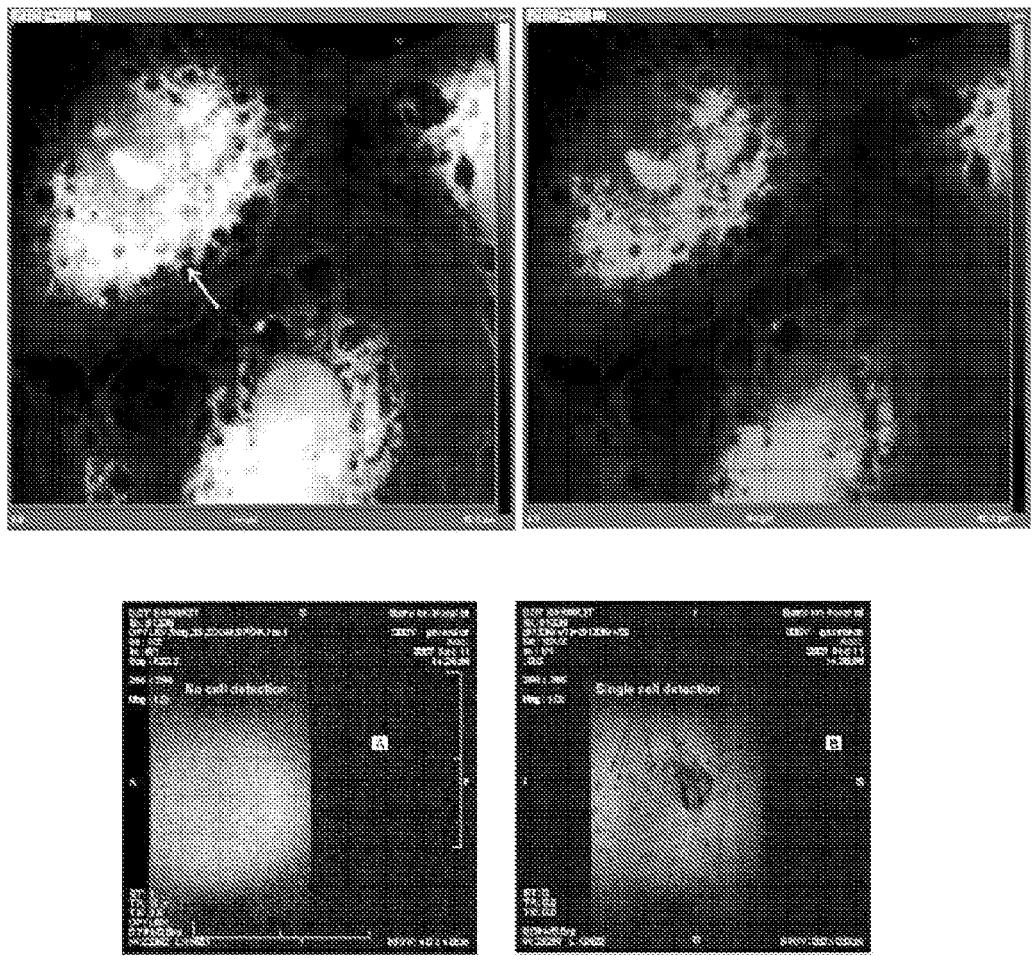
Figure 5:
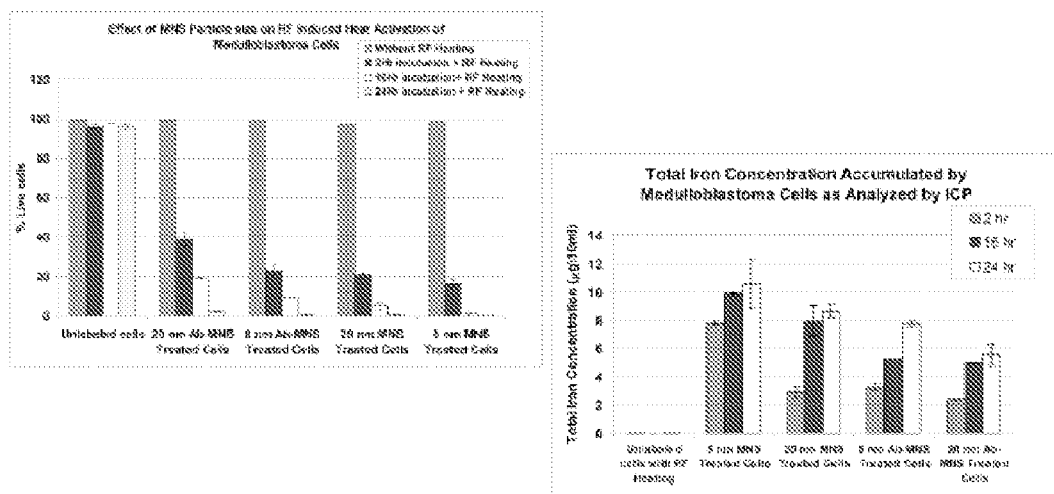
FIG. 5 shows in vitro RF induced thermal activation of medulloblastoma cells.
Figure 6:
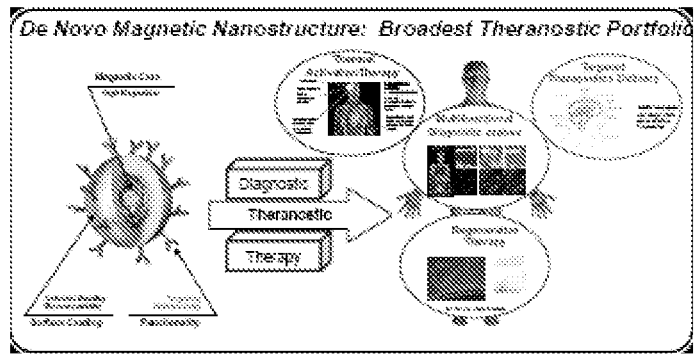
FIG. 6 shows an overview of targeting and therapeutic compositions of embodiments of the present invention.
Figure 7:
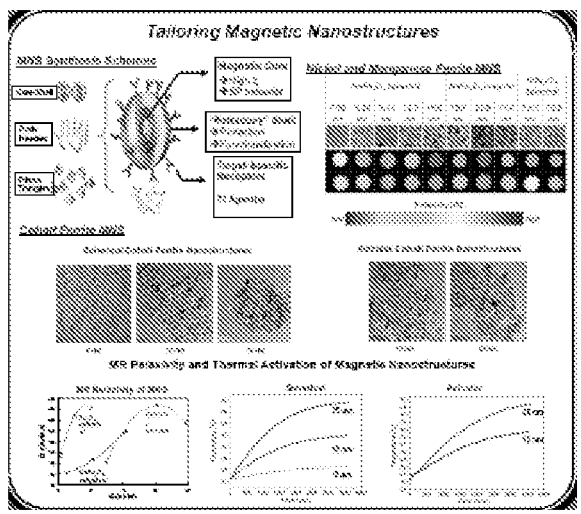
FIG. 7 shows targeting and therapeutic compositions of embodiments of the present invention.
Figure 8:
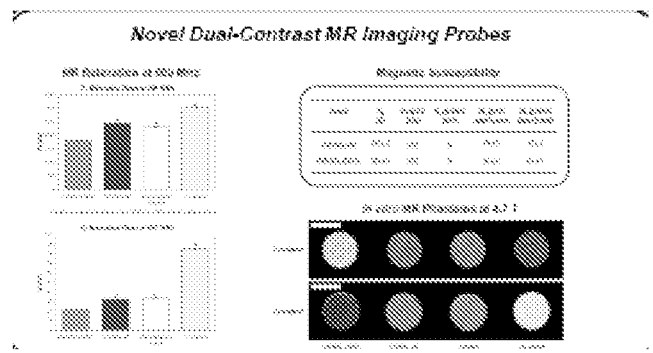
FIG. 8 shows dual-contract MRI probes of embodiments of the present invention.
Figure 9:
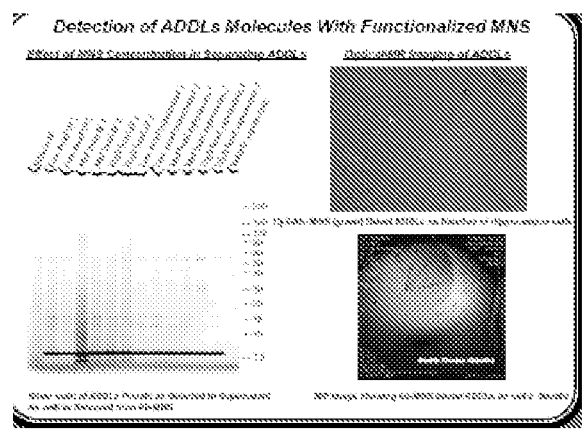
FIG. 9 shows detection of ADDLs molecules with functionalized MNS.
Figure 10:
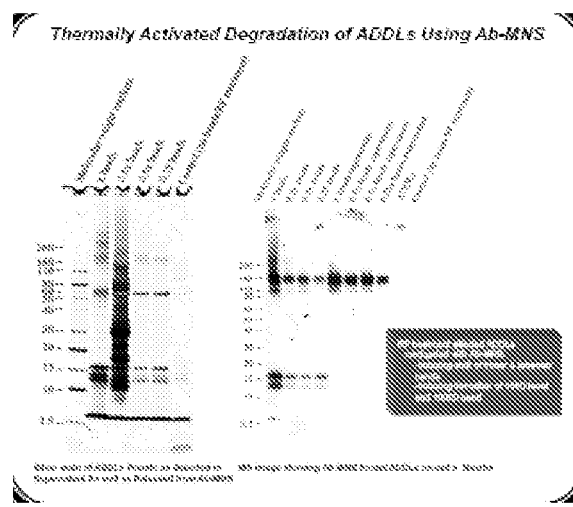
FIG. 10 shows thermally activated degradation of ADDLs using Ab-MNS.
Figure 11:
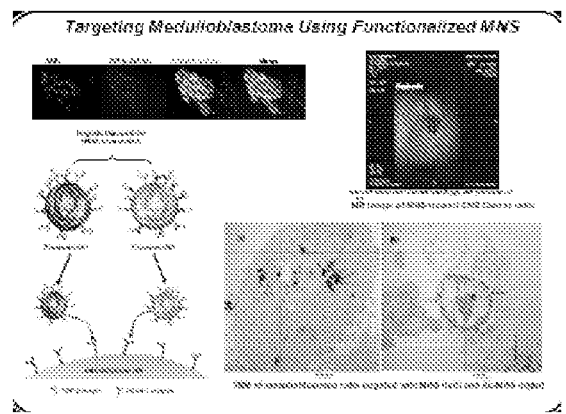
FIG. 11 shows targeting of medulloblastoma using functionalized MNS.
Figure 12:
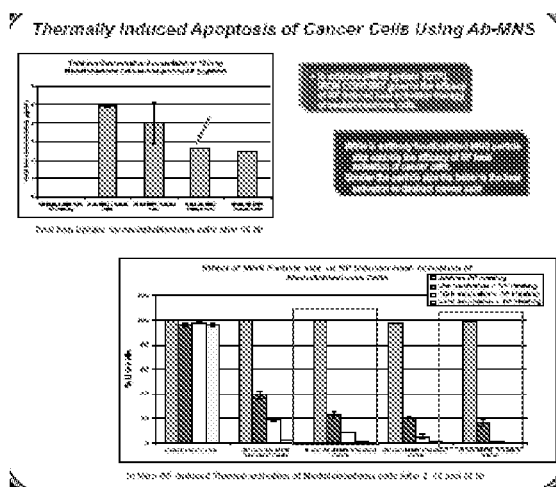
FIG. 12 shows thermally induced apoptosis of cancer cells using Ab-MNS.
Figure 13:
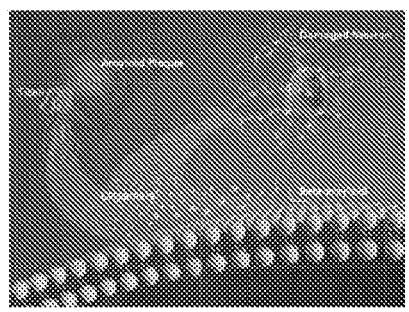
FIG. 13 shows a diagram of Aβ oligomers binding to synapses of hippocampal cells.
Figure 14:
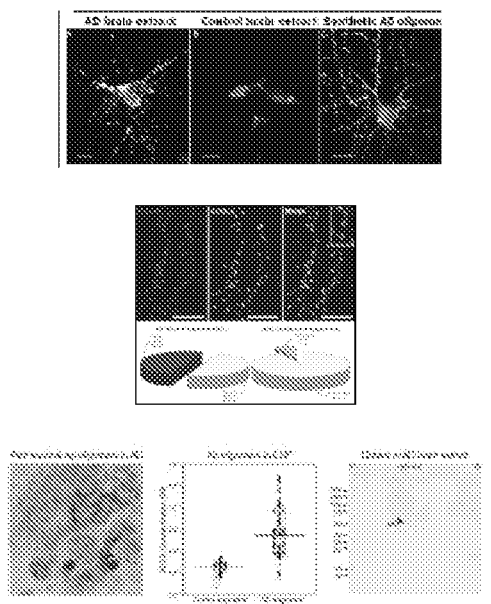
FIG. 14 shows Top) Aβoligomers are diffusible ligands that bind to primary hippocampal neurons in a punctate manner. (Middle) Aβoligomers bind at synapses (>50%). (Bottom) Aβoligomers are found in human tissue [left—human brain slice; middle—human CSF; right—human brain extract] and are clinically relevant.
Figure 15:
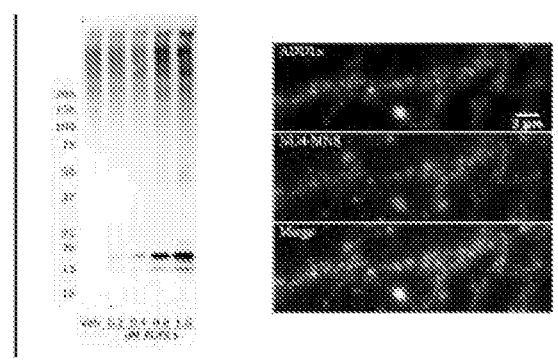
FIG. 15 shows (Left) Western blot analysis of increasing concentrations of Aβ oligomers (ADDLs) isolated from solution using Ab-MNS demonstrates that the Ab-MNS bind to and isolate Aβ oligomers proportional to the amount present. (Right) Co-localization studies using FITC-conjugated Aβ oligomers and Cy5 to localize the Ab-MNS show that nearly all of the Aβ oligomers present were also bound by the Ab-MNS.
Figure 16:
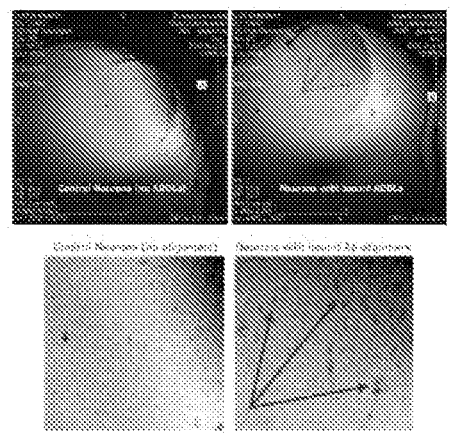
FIG. 16 shows (Top) MRI images of Ab-Magnetic nanostructures bound to Aβoligomers (ADDLs) on neurites. (A) Control cells without Aβoligomers and 0.5 mg Ab-MNS (Vehicle control). (B) The black dots represent the presence of Ab-MNS (0.5 mg) labeled Aβoligomers on neurites. (Bottom) Centers of circular sections magnified to better show labeling.
Figure 17:
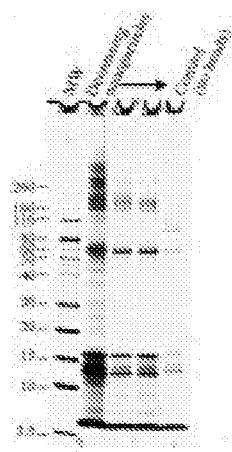
FIG. 17 shows silver stain showing the low molecular weight degradation products of Aβ oligomers as released from Ab-MNS after 1 hr exposure to Radio frequency (Rf)-induced thermal activation.
Figure 18:
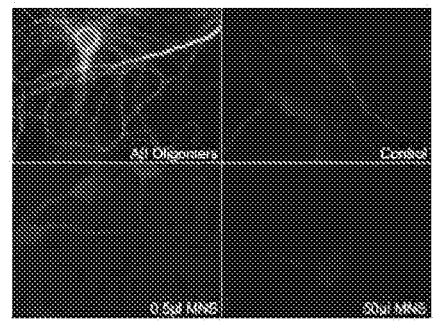
FIG. 18 shows that a tau phosphorylation toxicity assay revealed Rf-induced thermal inactivation of Aβ oligomers by Ab-MNS. (Top left) Aβ oligomers without Ab-MNS or Rf heating, a positive control. (Top right) Control (media), negative control. (Bottom left) Aβ oligomers+0.5 mg/ml Ab-MNS. (Bottom right) Aβ oligomers+50 mg/ml Ab-MNS.
Figure 19:
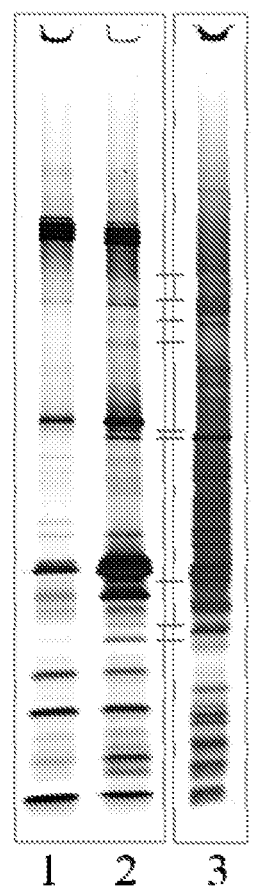
FIG. 19 shows selective capture of synaptosome protein by ADDL mag-beads.
Figure 21:
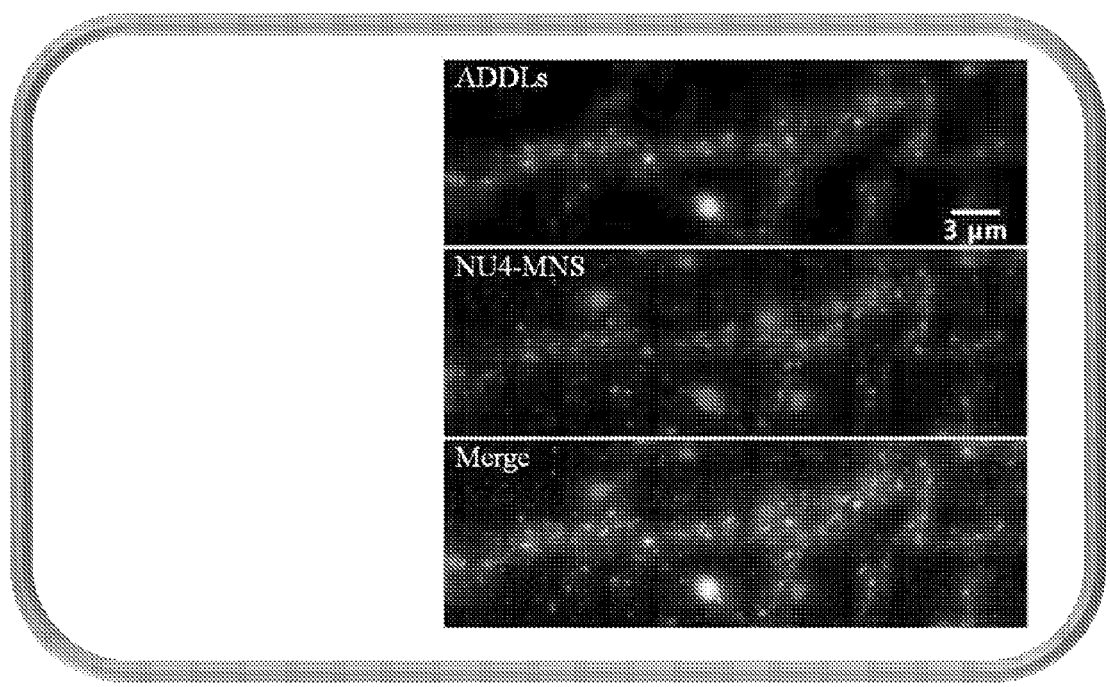
FIG. 21 shows that magnetic nanostructutres colocalize with ADDLs on neuritic spines.
Figure 23:
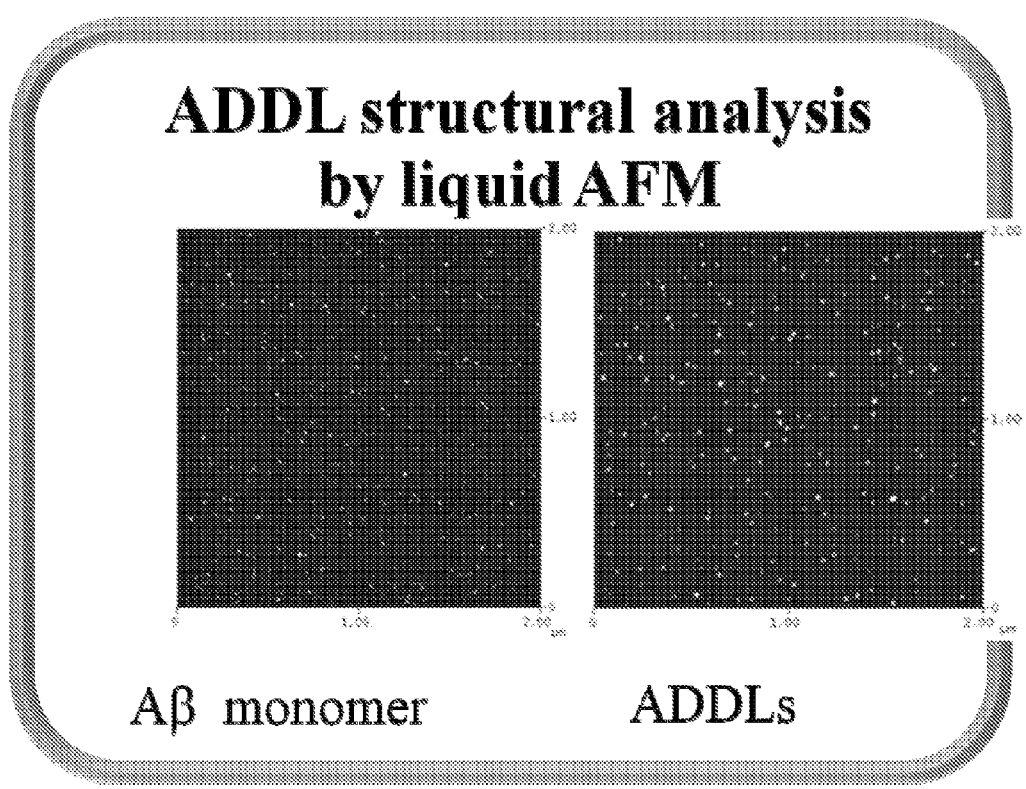
FIG. 23 shows ADDLs structural analysis by liquid AFM.
Figure 24:
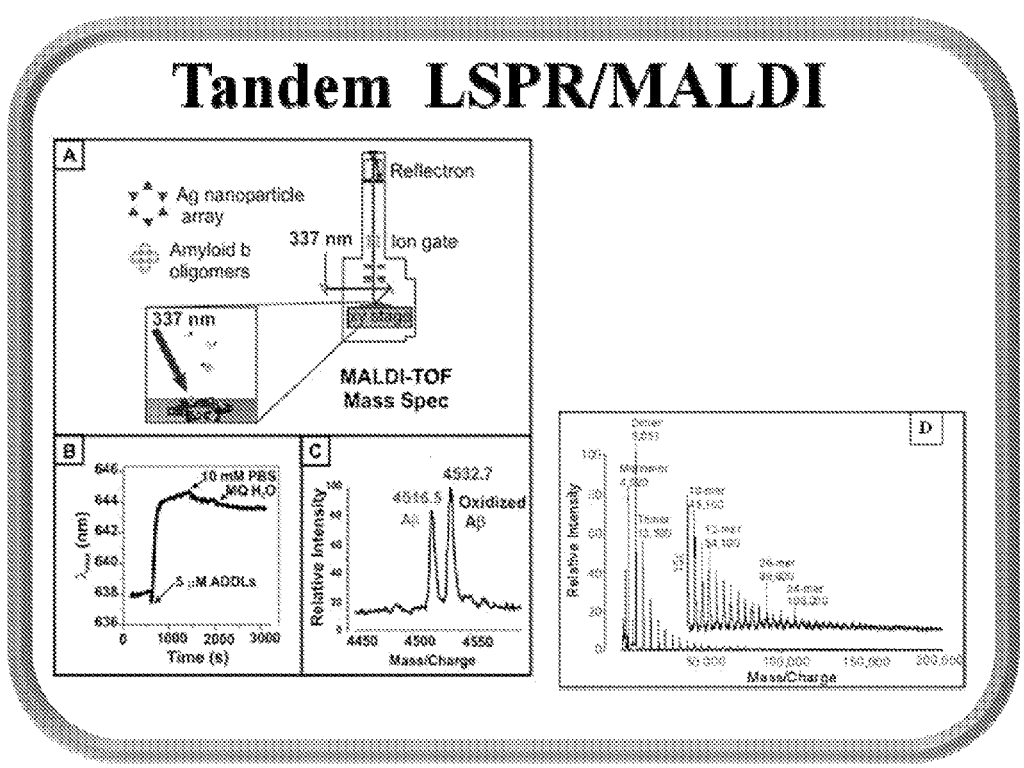
FIG. 24 shows tandem LSPR/MALDI using compositions of embodiments of the present invention.
Figure 25:
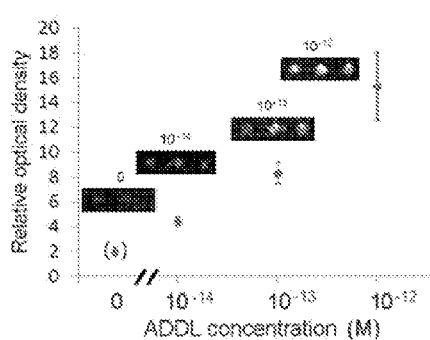
FIG. 25 shows development of scannimmuno assays for ADDLs.
Figure 25:
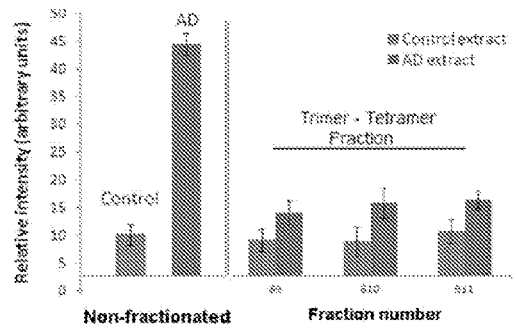
Figure 26:
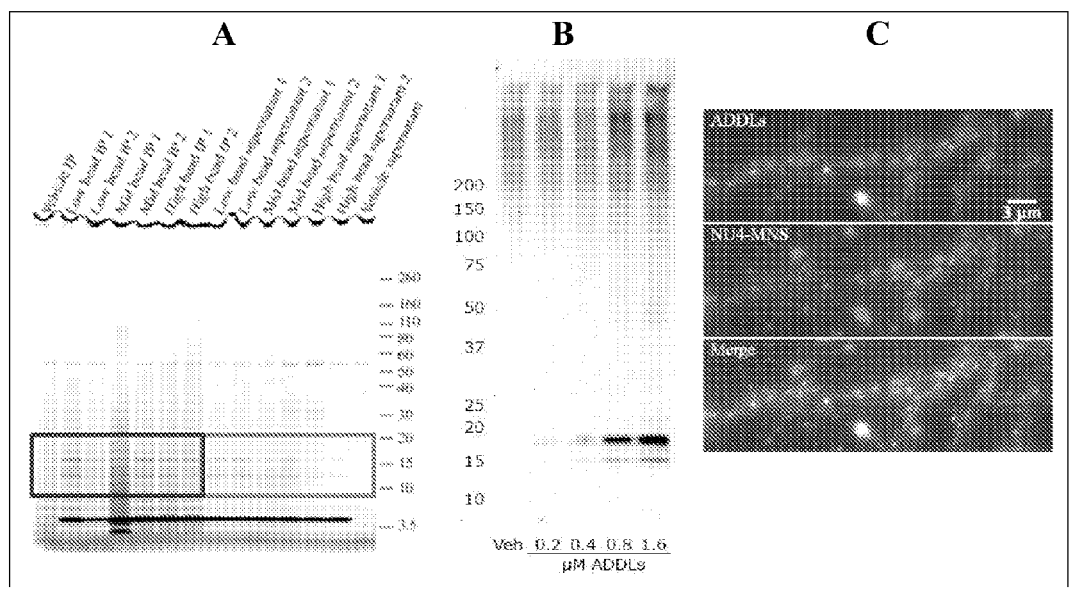
FIG. 26 shows (A) Silver staining analysis of ADDL proteins as detected in unbound supernatant as well as released from Ab-MNS. (B) Western blot analysis of increasing concentrations of ADDLs isolated from solution using Ab-MNS demonstrates that the Ab-MNS bind to and isolate ADDLs proportional to the amount present. (C) Co-localization studies using FITC-conjugated ADDLs and Cy5 to localize the Ab-MNS show that the ADDLs present were also bound by the Ab-MNS.
Figure 27:
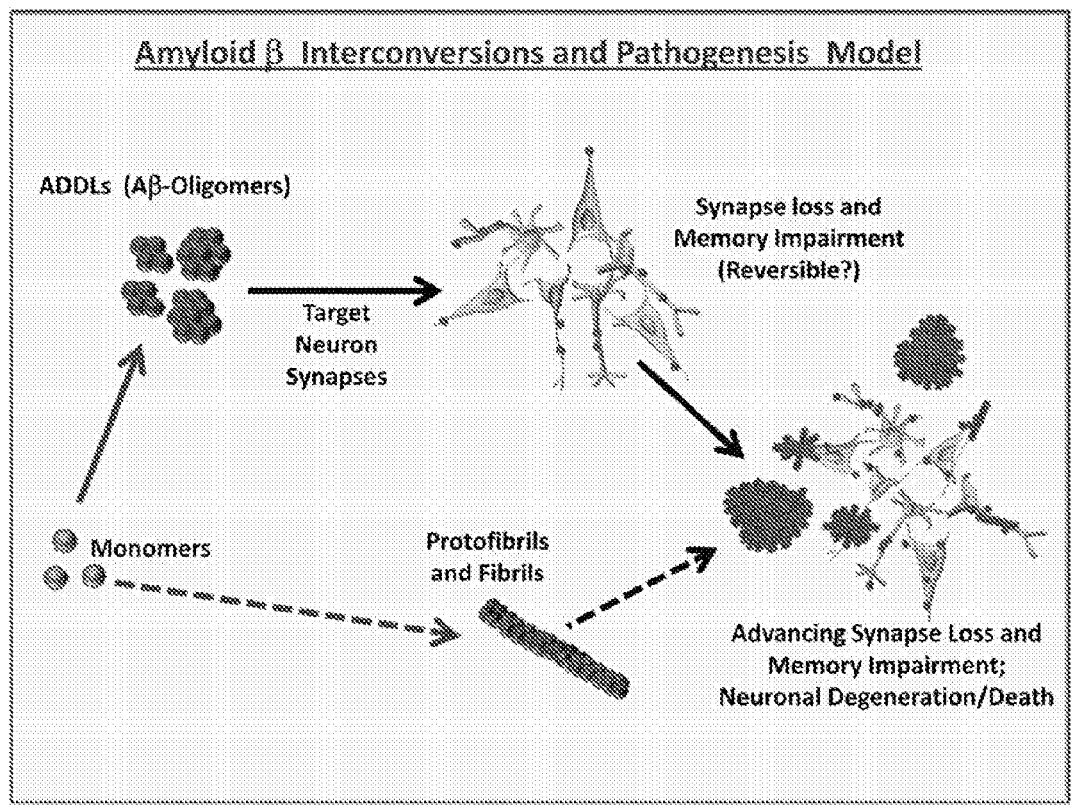
FIG. 27 shows a schematic illustration of ADDLs, once formed, bind to synapses of hippocampal cells which results in loss of synaptic plasticity followed by synapse loss, memory impairment, and ultimately neural death.

During experiments conducted during the course of development of embodiments of the present invention, it was demonstrated that synthesized theranostic agent can selectively target surface markers of medulloblastoma. To validate this, colocalization experiments were performed to target TGFβ and NCAM surface receptors simultaneously (FIG. 3).

In other embodiments, the present invention provides targeted therapy for Alzheimer's disease. In some embodiments, the present invention provides highly specific anti-Aβ-oligomer (anti-ADDL) antibodies and magnetic nanostructures for targeting and treating Alzheimer's disease.

Alzheimer's disease has long been associated with the formation of amyloid plaques and microtubule tangles. Recently it is discovered that a small protein, referred to as "ADDLs," binds to neurons and disrupts synaptic plasticity, leading to synapse loss, memory impairment, and ultimately memory loss. This theory gained momentum with an experiment where it was discovered that the neurons of mice function normally once the ADDLs were removed. Embodiments of the present invention use magnetically active theranostic nanostructures which can detect ADDLs at low concentration and can simultaneously degrade them into non-toxic ADDLs or low molecular weight by-products.

During the course of development of embodiments of the present invention, experiments demonstrated that Ab-MNS exhibited excellent colloidal stability and efficient thermal activation effect upon exposure to an alternating radio frequency, which is non-invasive to non-magnetic materials. These Ab-MNS effectively recognize and target ADDL oligomers at fmol concentration in solution as well as on hippocampal cells. This was later verified using fluorescence microscopy and a conventional MRI. Further, the efficiency of Radiofrequency induced thermal activation of ADDLs by Ab-MNS was monitored. It was demonstrated that these molecularly targeted theranostic agents can absorb radio frequency and generate heat which is sufficient to either completely transform neurotoxic ADDLs to non-toxic forms and\or low molecular weight by-products. A Tau hyperphosphorylation-based toxicity assay further confirms the preeminence of Ab-MNS system over control (without Ab-MNS). Because these nanostructures are selectively bound to the ADDLs, they can target ADDLs proteins without causing harm to the neuron.

The approach of localization of MNS, associated MRI imaging and thermal activation to locally heat and breakdown molecular product is applicable to not just ADDLs and related proteins. It is also useful for any other similar diseases where localized molecular species are responsible for specific disease. Further, in the event alternative or complementary biomolecular structures are shown to be responsible for Alzheimer's (or other diseases), the MNS localized for MRI and thermal therapy also apply.

Figure 29:
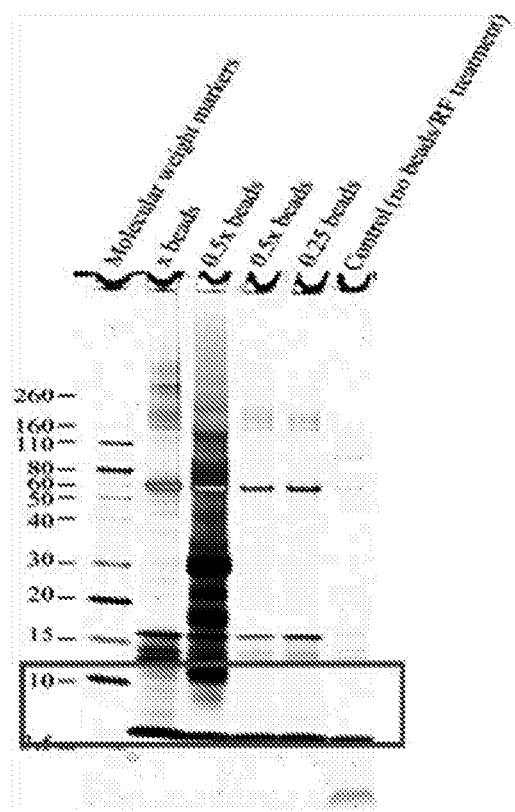
FIG. 29 shows silver stain showing the low molecular weight degraded products of ADDLs protein as released from Ab-MNS after 1 hr exposure to Rf induced thermal activation.
Figure 30:
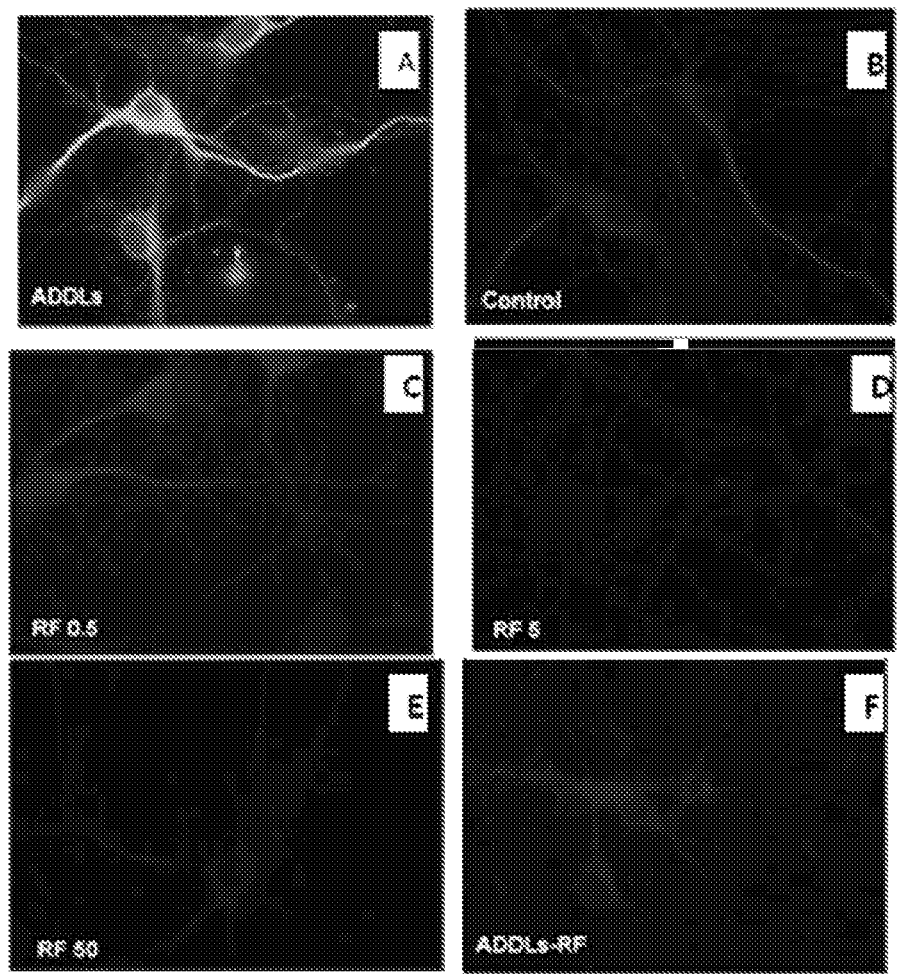
FIG. 30 shows that a tau phosphorylation toxicity assay revealed Rf-induced thermal inactivation of ADDLs by Ab-MNS. A) ADDLs without Ab-MNS, no Rf heating, B) Control (media), C) ADDLs+0.5 µg\ml Ab-MNS, D) ADDLs+5 µg\ml Ab-MNS, E) ADDLs+50 µg\ml Ab-MNS, F) ADDLs+ Rf Heating.
Figure 31:
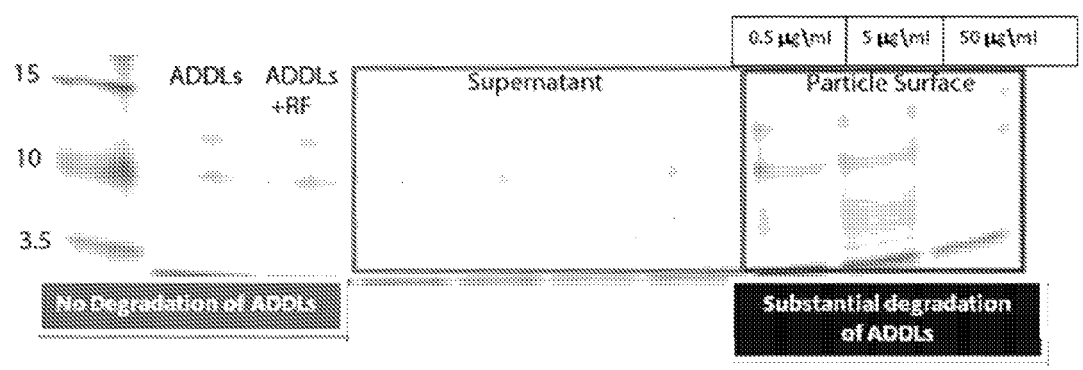
FIG. 31 shows silver stain showing the low molecular weight degraded products of ADDLs protein as released from Ab-MNS after 1 hr exposure to Rf induced thermal activation as shown in box.

Embodiments of the present invention provide optimum doses of theranostic MNS capable of selectively binding to the target protein, ADDLs, and further capable of generating sufficient but localized heat to degrade bound proteins using an otherwise non-invasive application of an AC field generated by an radio frequency (RF) generator. Experiments conducted during the course of development of embodiments of the present invention demonstrated the ability of the MNS theranostic probes to degrade neurotoxic ADDLs to non-toxic low molecular weight products (FIG. 29). The efficacy of Rf induced thermal ablation of ADDLs was further confirmed using a toxicity assay in which Tau protein phosphorylation induced by ADDLs was measured (FIG. 30). Similar approaches are undertaken for other biomolecular species and/or other diseases which require local non-invasive imaging probe and localized thermal degradation of biomolecular species.

Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. For example, in some embodiments dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. In some embodiments, following successful treatment, the subject undergoes maintenance therapy to prevent the recurrence of the disease state.

III. Diagnostic Applications

In some embodiments, the present invention provides compositions and methods for diagnostic applications. For example, in some embodiments, diagnostic applications are used to image and define tumor boundaries. Such images find use, for example, prior to and during surgical removal of brain tumors and for therapeutic targeting of tumors. In other embodiments, compositions and methods are used in the targeting of ADDLs in the diagnosis and treatment of Alzheimer's disease. The compositions and methods described above are suitable for use in diagnostic applications.

In some embodiments, nanoparticles comprise a contrast agent for imaging (e.g., X-Ray, computer tomography (CT) imaging, or MRI imaging). In some embodiments, nanoparticles comprise imaging targeting moieties (e.g., nucleic acids, PNAs, peptides, proteins, antibodies, etc.) that target the conjugates to a region of interest (e.g., tumor).

In some embodiments, nanoparticles are used in research (e.g., imaging in animal models, structural studies, DNA-protein binding interactions, protein capture, etc.) or drug screening applications.

Experiments conducted during the course of development of the present invention demonstrated that functionalized magnetic nanostructures (8 nm to 20 nm) enables the combined discovery\diagnosis and therapy of malignant medulloblastoma cells. Particles were synthesized and then functionalized, for example, with antibody against TGF-β (transforming growth factor) surface receptor which is over expressed by the medulloblastoma cells. The cell viability experiments shows biocompatibility of using Ab-MNS with no observed toxicity to the medulloblastoma (contact time 1 hr). The synthesized Ab-MNS was very effective in targeting the surface receptor and is highly biocompatible.

In some embodiments, the present invention provides a multimodel imaging platform for the early detection of medulloblastoma. Medulloblastoma cells are labeled with Ab-MNS and imaged using TEM, SEM, or AFM. In some embodiments, the theranostic agent labeled cells are also imaged with high-precision using a clinical MRI system. The tumor can be detected at as low as single cell level. In some embodiments, the theranostic agents include magnetic nanostructures of 8 nm to 20 nm that have the ability to seek and label a tumor marker. Utilizing the antibody functionality these theranostic nanostructures overcome the issues associated with the delivery of conventional contrast agents to a site of interest such as a tumor. One other advantage these theranostic nanostructure have is shorter effective transverse relaxation time (T2) of tissue that take up or are labeled with these nanostructures. This results in intensity enhancement as compared to the most conventional contrast agents, which have poor specificity and contrast.

In some embodiments, the present invention provides diagnostic assays for Alzheimer's disease. In some embodiments, assays utilize MNS covalently attached with an anti-ADDLs antibody as a targeting moiety.

Figure 28:
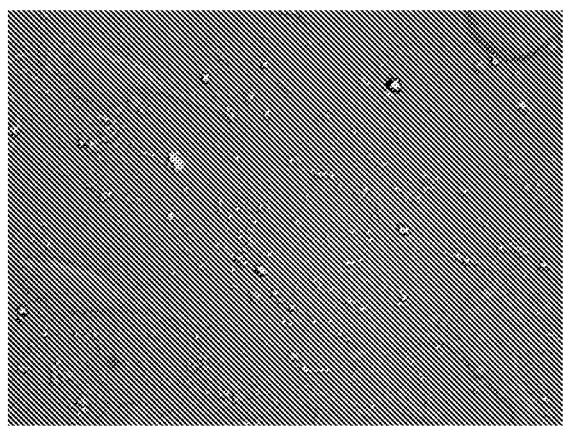
FIG. 28 shows a) detection of ADDLs on neuritis of hippocampus cells; b) Ab-MNS enhanced MRI mapping of ADDLs proteins bound with neurite; c) high resolution image of ADDLs detected by liquid AFM.
Figure 28:
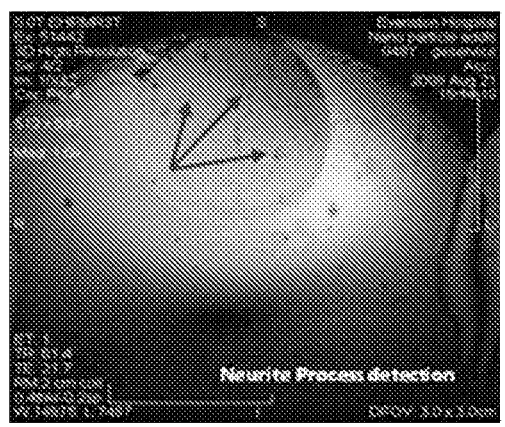
Figure 28:
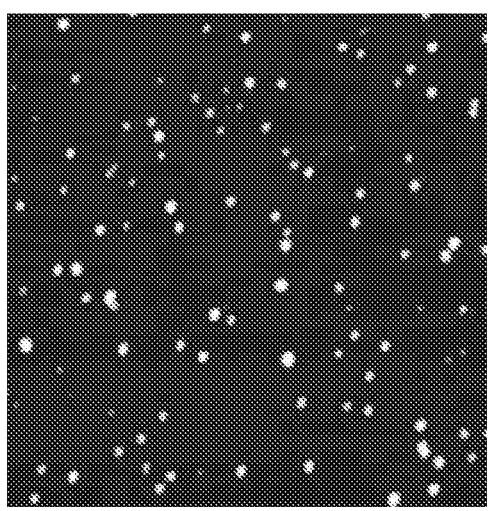

Embodiments of the present invention provide compositions and methods for selectively targeting ADDL proteins at low concentrations, so that the ADDLs can be identified with high-precision, using traditional fluorescence microscopy (FIG. 28a) for in-vitro studies, conventional non-invasive MRI system (FIG. 28b) for in-vivo diagnostics, and the-state-of-art advanced microscopy (AFM) (FIG. 28c) for in-vitro. In some embodiments, the theranostic agents are comprised of magnetic nanostructures covalently conjugated to an ADDLs-specific antibody that has the ability to selectively target ADDLs bound to synapses on the neuron. Utilizing the antibody functionality, these theranostic nanostructures overcome the issues associated with the delivery of conventional contrast agents to a site of interest such as an ADDLS bound neurite. Thus, embodiments of the present invention provide the earliest possible detection of Alzheimer disease using a clinical imaging system e.g., MRI.

IV. Kits and Systems

In some embodiments, the present invention provides kits for using in research, diagnostic and therapeutic applications. In some embodiments, kits include components necessary, sufficient or useful in performing the methods of embodiments of the present invention.

In some embodiments, kits include drug-targeting molecule compositions, MNS, along with any controls, buffers, reagents, administration tools, etc.

Kits may further comprise appropriate controls and/or detection reagents. Any one or more reagents that find use in any of the methods described herein may be provided in the kit.

In some embodiments, the present invention provides systems for use in targeting and treating tumors and Alzheimer's disease. In some embodiments, systems comprise the above described components and a device for generating a radio frequency (RF) for use in therapy of tumors and Alzheimer's plaques.

V. Antibodies

The present invention provides isolated antibodies. In preferred embodiments, the present invention provides monoclonal antibodies that specifically bind to an isolated polypeptide comprised of at least five amino acid residues of target of embodiments of the present invention (e.g., cell surface markers associated with CNS cancers or Alzheimer's disease). These antibodies find use in the diagnostic and therapeutic methods described herein.

In some embodiments, known antibodies are utilized. For example, in some embodiments, NU-4 is use to target MNS to ADDLs.

An antibody for use in embodiments of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% CO2 gas. The antibody titer of the supernatant of a hybridoma culture can be measured according to the same manner as described above with respect to the antibody titer of the anti-protein in the antiserum.

Separation and purification of a monoclonal antibody (e.g., against a marker described herein) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

EXPERIMENTAL

The following examples are provided in order to demonstrate and further illustrate certain preferred embodiments and aspects of the present invention and are not to be construed as limiting the scope thereof.

Example 1

1. Conjugation Protocol for Antibody with MNS:
Amino-functionalized magnetic nanostructures were synthesized following a three step protocol:
   A) Sulfhydryl Modification of Amine-Functionalized MNS
Reagents and Materials:
N-succinimidyl-S-Acetyl-Thioacetate (SATA—Pierce biotechnology, Product number 26102)
Hydroxylamine.HCl (Product No. 26103)
Phosphate Buffered Saline (PBS, Product No. 28372)
EDTA and 1 N NaOH for modifying PBS buffer
DMSO (Dimethylsulfoxide, Product No. 20688)
Buffer Preparation:
Reaction Buffer Prepare 200-500 ml of PBS: 0.1 M phosphate, 0.15 M NaCl, pH 7.2-7.5
Deacetylation Solution 0.5 M Hydroxylamine, 25 mM EDTA in PBS, pH 7.2-7.5. Dissolve 1.74 g hydroxylamine.HCl and EDTA (0.475 g of tetrasodium salt or 0.365 g of disodium salt) in 40 ml of Reaction Buffer. Add ultrapure water to a final volume of 50 ml and adjust pH to 7.2-7.5 with NaOH.
After 2h Deacetylation Solution 10 ml reaction buffer containing 10 mM EDTA and adjust pH to 7.2-7.5 with NaOH.

Procedure:
Immediately before reaction dissolve 2 mg of SATA in 200 µl of DMSO.
Combine 1 ml of MNS solution with 25 µl of the SATA solution.
Mix contents and incubate reaction at room temperature for 30 min under constant shaking
After completion of the reaction separate MNS by magnet and remove the supernatant.
Wash MNS 3× using reaction buffer and magnetic separation
Add 1 ml of deacetylation solution and incubate the reaction for 2 hr at room temperature.
After 2 hr deacetylation decant the solution via magnetic separation and add after 2 hr solution containing 10 mM EDTA in reaction buffer. (this step is preferably performed immediately before adding sulfo-SMCC modified Antibody solution).

B) Two Step MNS-Antibody Cross-Linking Procedure
Reagents and Materials:
Sulfosuccinimidyl 4-[N-maleimidomethyl]cyclohexane-1-carboxylate sulfo-SMCC—Pierce biotechnology, Product number 22322)
Zeba Desalt Spin Columns, 5×2 ml columns for desalting 200-700 µl samples (Product No. 89889)
Buffer Preparation:
Reaction Buffer Prepare 200-500 ml of PBS: 0.1 M phosphate, 0.15 M NaCl, pH 7.2-7.5
Conjugation Solution phosphate-buffered saline (PBS=100 mM sodium phosphate, 150 mM sodium chloride, pH 7.2; e.g., Product No. 28372) add EDTA to 1-5.
Procedure:
Dissolve 2 mg of sulfo-SMCC in 200 µl of conjugation buffer.
Add 20 µl of sulfo-SMCC solution to the 1 ml of Antibody solution (0.5 mg/ml concentration).
Mix contents and incubate reaction at room temperature for 30 min under constant shaking
After completion of the reaction remove excess crosslinker using a desalting zeba column equilibrated with conjugation buffer.

C) Two Step MNS-Antibody Crosslinking Procedure
Procedure:
Add equal volume of sulfhydryl modified MNS with sulfo-SMCC modified antibody.
Incubate for 1 hr.
Magnetic separation and resuspend Ab-MNS in reaction buffer and store at 4 C till use.

2. Information About Antibodies
Antibodies used in these investigation were purchased from R&D system Inc.
a) TGF-b (Product No FAB241P)
Phycoerythrin (PE)-conjugated monoclonal anti-human TGF-β RII: Supplied as 25 µg of antibody in 1 µL saline containing up to 0.5% BSA and 0.1% sodium azide.
Clone #: 25508
Ig class: mouse $IgG_1$
Storage
Reagents are stable for twelve months from date of receipt when stored in the dark at 2°-8° C.
b) NCAM-1
Catalog Number: MAB24081
Clone: 301021
Lot Number: XSR01
Size: 100 µg
Formulation: 0.2 µm filtered solution in PBS with 5% trehalose
Storage: −20° C.
Reconstitution: sterile PBS
c) CD133
Catalog Number: ab5558 from AbCAM
Size: 100 µg
Storage: 4° C.
Reconstitution: sterile PBS 3. MR Imaging
Agarose phantoms of dispersed labeled cells were prepared as follows. After labeling and washing with 0.1M cacodylate buffer, the cells were fixed for 1 h at room temperature in 4% paraformaldehyde and washed again with PBS buffer. Cells were fixed for better stability of the sample. Cell pellets containing known numbers of labeled and unlabeled cells were gently mixed with 1 ml of low-melting-point 0.3% agarose gel at 35° C. Three series were prepared. The 'cell density' series consisted of a total of $0.02×10^6$ and $1.0×10^6$ B9 cells in 1 ml of agarose labeled with (40 µg/ml of MNS and Ab-MNS). The 'labelling series' was composed of 1 ml of agarose gel containing $0.02×10^6$ and $1.0×10^6$ B9 cells labeled with MNs and Ab-MNS of particle size 8 nm and 25 nm. Finally the control comprising similar concentration of MNS, Ab-MNS, unlabeled cells, and agarose gel. Single cell detection experiments were conducted using Ab-MNS labeled and unlabeled cells grown in single well camber slide. Cells were fixed as mentioned above followed by pouring a layer of 0.3% agarose gel on top.

MRI was performed on a short bore of 3.0 T Twin Speed scanner with Excite technology (General Electric Medical Systems, Milwaukee, Wis., USA) using a home built 2 cm surface coil. A 3 D fast gradient echo sequence was used to image the gel samples with cells (TR/TE/FA=17.4/3.5 ms/10o/20 slices with 0.7 slice thk/4 FOV/256×256 Matrix). For T2 mapping, a 2D multiecho spin echo sequence (TR/TE 1000 ms/6.2, 12.4, 18.6, 24.8, 31.0, 37.2, 43.4, 49.6 ms/3 mm sl thk/320×256 Matrix/24×24 FOV) was used. $T_2$ maps were constructed on an Advantage Workstation (General Electric Medical Systems, Milwaukee, Wis., USA) using the FUNC-TOOL program by fitting a single exponential function to the signal intensity vs echo time data. T2 values were read by defining regions of interest within each sample.

4. Thermal Activation Therapy
An alternating magnetic field (AMF) heating system was purchased from MSI Automation, Inc. (Wichita, Kans., USA). The experiment was performed inside a copper coil (diameter 10 cm), which produces an AMF at a fixed frequency of 300 kHz and amplitude ranging from 0-18 kA m$^{-1}$. The temperature of the sample holder was maintained at 37° C. by using a deltaphase isothermal pad. A single temperature probe with a diameter of 0.55 mm of a 4-channel fiberoptic thermometry device (Luxtron Corp. Santa Ana, Calif., USA) was used to monitor the temperature rise.

4. MNS composition
For initial experiments,
Iron oxide, 8 nm particle size, was used in ADDLs experiments.
Iron oxide of 8 nm and 20 nm size was used in Medulloblastoma experiments.

Example 2

Figure 32:
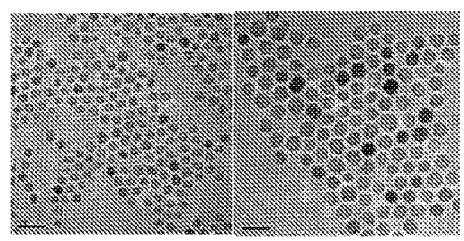
FIG. 32 shows magnetic nanostructures synthesized by chemical decomposition method followed by seed mediated growth process.

Synthesis of Spherical Magnetic Metal Oxide Nanostructures:
Nanostructures of different sizes were synthesized by seeded-growth thermal decomposition. Iron acetylacetonate (4 mmol) and metal acetylacetonate (2 mmol) (for binary oxides while for ternary and higher compositions depending on the ratio of metal ion precursor) were used as a precursor to make $MFe_2O_4$ nanostructures. Three surfactants, dodecylamine (12 mmol), lauric acid (12 mmol), and 1,2-hexadecanediol (20 mmol) were added to stabilize nucleation and growth. Benzyl ether (40 ml) was used as the solvent. The solution was heated to 230° C. for 2 hours with a flow of nitrogen gas to prevent oxidation, and then raised to 280° C. for 1 hour. The resulting nanostructure diameters were 5 to 7 nm (FIG. 32). The magnetic nanostructures were precipitated out from the solvent through external magnetic field as well as with addition of alcohol.

To grow larger particles, 60 mg of the nanostructure seed was mixed with iron acetylacetonate (0.57 mmol), metal acetylacetonate (0.29 mmol) (for binary oxides while for ternary and higher compositions depending on the ratio of metal ion precursor), dodecylamine (1.71 mmol), lauric acid (1.71 mmol), and 1,2-hexadecanediol (2.86 mmol) in benzyl ether (40 ml). In the growth reaction, the solution was heated directly to 280° C. for 3 hr without holding at 230° C. If desired, nanostructure size is further increased by repeating the growth reaction.

Example 3

Magnetic Nanostructure Immunoprecipitation Protocol

MNS are prepared for use in immunoprecipitating out ADDLs from solution by washing a desired volume of the Ab-MNS in PBS twice, sonicating and pelleting between washes. The resuspended Ab-MNS are then either treated with 5M NaOH for 1 minute followed by 3 washes with PBS as above or not and then blocked with 0.1% bovine serum albumin (BSA) for 45 minutes to 4 hours at 37° C. with rotation. After blocking, the Ab-MNS are washed with either PBS-0.1% BSA or F12-0.1% BSA and resuspended in this solution prior to adding ADDLs or control. The Ab-MNS are incubated overnight at 4° C. with rotation to allow maximum binding of ADDLs. The Ab-MNS are washed three times with PBS or F12 and then the suspension is transferred to a new tube for the next steps.

Thermal Activation Treatment (RF)

An alternating magnetic field (AMF) heating system was purchased from MSI Automation, Inc. (Wichita, Kans., USA). The experiment was performed inside a copper coil (diameter 10 cm), which produces an AMF at a fixed frequency of 300 kHz and amplitude ranging from 0-18 kA m$^{-1}$. The temperature of the sample holder was maintained at 37° C. by using a deltaphase isothermal pad. A single temperature probe with a diameter of 0.55 mm of a 4-channel fiberoptic thermometry device (Luxtron Corp. Santa Ana, Calif., USA) was used to monitor the temperature rise.

Elution

After immunoprecipitation with or without RF treatment, the Ab-MNS were pelleted and the supernatants transferred to clean tubes, marked as "supernatants" and saved for further analysis. The proteins bound to the Ab-MNS were eluted using Laemmli buffer diluted with PBS to 1:1 for 10 minutes. The samples are again pelleted, the supernatant material transferred to clean tubes and marked as "pellets" for further analysis.

SDS-PAGE

Samples, prepared by combing 2:1 Laemmli sample buffer (Bio-Rad), and prestained SDS-PAGE standards (Bio-Rad) were loaded into Novex 4-20% Tris-Glycine (Invitrogen), 1 mm, 15 well gels and electrophoresed at 125V until the tracking dye was at the bottom of the gel.

Silver Stain

To image all proteins present in a sample, a silver stain kit (Invitrogen) was used according to manufacturer's instructions. Briefly, after electrophoresis the gel was removed from the cassette and fixed. After rinsing in excess water twice, the gel was sensitized, stained, and developed.

Transfer and Western Blot:

After electrophoresis, the gel was removed from the cassette and equilibrated in cold transfer buffer (10% TG (Bio-rad), 20% Methanol, and 0.02% Sodium dodecyl sulfate (SDS). Hybond ECL nitrocellulose is also equilibrated in a separate container. The equilibrated gel and nitrocellulose are sandwiched together between two pieces of filter paper inside two fiber pads according to manufacturer's instructions (Bio-rad) and placed in the transfer apparatus. After filling the apparatus completely with the remaining transfer buffer, the transfer is run at 100V for 1 hr at 4° C. The nitrocellulose is collected and the remaining gel and filter paper discarded. The nitrocellulose is blocked in 5% non-fat dried milk (NFDM) in TBS-0.1% Tween 20 (TBS-T) for 1 hour at room temperature (RT) or overnight at 4° C. The primary antibody is diluted in 5% NFDM-TBS-T and incubated with the nitrocellulose for 90 minutes at RT. The nitrocellulose is washed 3×10 minutes with TBS-T and then incubated with diluted secondary antibody (HRP-linked anti-mouse or anti-rabbit IgG (Amersham) diluted in 5% NFDM-TBS-T) for 1 hour at RT. After rinsing 3 times with TBS-T and 3 times with ddH$_2$O, the SuperSignal West Femto Maximum Sensitivity Substrate (Pierce) was used according to manufacturer's instructions to visualize the protein bands and imaged either on film or using the Kodak ImageStation (Kodak).

Immunolabeling and Immunofluorescence:

Primary hippocampal cultures, aged 14-32 days in vitro (d.i.v.) were used for all immunolabeling and immunofluorescence assays. Cells were grown in NbActiv media (Brain-Bits) until use.

ADDL Incubation:

The coverslips with cells growing on one side were transferred, cell side up, to 24-well plates and an equal volume of conditioned media (media the cells had been growing in) containing either ADDLs. A FITC-conjugated ADDL preparation was used or vehicle was added to each well. The cells were incubated at 37° C. for 30-45 min.

Fixation:

After incubation, the cells were rinsed with warm conditioned media, Neurobasal media, or a combination of both 3 times rapidly to remove unbound ADDLs. The cells were then fixed by adding a volume of warm 3.7% formaldehyde (in PBS) to the volume of media in each well and allowing it to sit at RT for 5 mins. The media/formaldehyde was completely removed to a waste bottle and replaced with a volume of 3.7% formaldehyde for 5 minutes at RT. The cells were then rinsed with PBS 3 times for at least 5 mins each and then stored in PBS until use.

Immunolabeling with Ab-MNS:

Cells were blocked in 10% normal goat serum (NGS)/PBS for 30-45 minutes at RT. The cells were then incubated with diluted Ab-MNS (1-10 µg maximum possible antibody/ml) on a rocker or orbital shaker at RT for 2-3 hours or at 4° C. overnight. The cells were washed 3 times for 5 minutes each with PBS. AT this point the Ab-MNS were processed either for immunofluorescence or for MR imaging.

Immunofluorescence:

After incubation with the Ab-MNS, the cells were then incubated with AlexaFluor 488 or AlexFluor 635 goat anti-mouse secondary antibody diluted 1:2000 in 1% NGS/PBS for 1-2 hours at RT. The cells were then rinsed 3 times for 5 minutes each with PBS and mounted, cell side down, on glass microscope slides using Prolong mounting reagent (Invitrogen). The slides were allowed to air dry in a light-protected box until the mounting media was solid (typically between 12-48 hours). The fluorescence was imaged using a Nikon epifluorescence microscope with MetaMorph software and quantified using ImageJ (NIH). For images, the fluorescence image captured was overlaid on the corresponding DIC image so that one could visualize the whole cell and where the Ab-MNS actually localized to on that cell.

Liquid AFM

APTES was prepared by diluting 3 µl of glacial acetic acid into 50 ml double distilled water and adding 500 µl APTES (Sigma). Mica discs were then incubated with the APTES solution in a glass beaker for 15 min at RT with slow shaking. After rinsing 6 times with double distilled water, the discs were dried and baked at 100° C. for 2 hours in a glass petri dish. The discs were stored in desiccators until used. The solution to be tested (90-100 µA) was then carefully placed on the disc and allowed to incubate for 15-30 minutes before buffer (F12, 10 ml) was added to the dish, covering the mica.

AFM observations were carried out using the Veeco BioScope II integrated with NanoScope V controller. Imaging was performed under wet ambient conditions at 25° C. using very sharp silicon probes (in tapping mode) attached to soft silicon nitride (SiN) cantilever with no reflecting coating on its back side (Spring constant ~0.035 N/m and resonant frequency around 17 KHz). These especially designed probes were manufactured by Applied Nanostructures Inc. (model number HYDRA6V200W). A silicon pad underneath the tip was used to reflect the laser, thus eliminating the need for metal coating and reducing the bimorph effect, as well as facilitating instant imaging without waiting to stabilize the probe in solution. Best imaging results were obtained in the frequency range corresponding to a broad maximum of cantilever oscillation amplitude around 12 KHz. Typical scan rates were very slow (0.5-0.8 Hz) with very precise feedback gains to minimize the noise.

Tau Hyper-Phosphorylation Assay:

Cells were cultured as detailed above. Cells were incubated with ADDLs, vehicle, or the fragments generated from Ab-MNS immunoprecipitated ADDLs that had been RF treated for 3-4 hours. Cells were then fixed as described above. Cells were blocked in 10% NGS/0.1% Triton X-100/PBS for 30-45 minutes at RT. The cells were then incubated with diluted anti-Tau pSer404 (1:500) in 10% NGS/0.1% Triton X-100/PBS at RT for 3 hours. The cells were washed 3 times for 5 minutes each with PBS. After incubation, the cells were then incubated with AlexaFluor 488 goat anti-rabbit diluted 1:2000 in 1% NGS/PBS for 1 hour at RT. The cells were then rinsed 3 times for 5 minutes each with PBS and mounted, cell side down, on glass microscope slides using Prolong mounting reagent (Invitrogen). The slides were allowed to air dry in a light-protected box until the mounting media was solid (typically between 12-48 hours). The fluorescence was imaged using a Nikon epifluorescence microscope with MetaMorph software and quantified using ImageJ (NIH).

ADDL Preparation

ADDLs are prepared using a known protocol. Oligomers are prepared according to a previously published protocol (Klein, Neurochem Int, 2002). Briefly, solid amyloid β peptide (Aβ1-42, American Peptide) is monomerized in HFIP (hexafluoro isopropanol), aliquoted, evaporated, and stored as a solid film at −80° C. The day before the experiment, the peptide film is resuspended in anhydrous dimethyl sulfoxide (Sigma-Aldrich) to make a 5 mM solution. The 5 mM peptide stock is then brought to 100 µM with the addition of F12 medium without phenol red (Caisson Laboratories). The solution is vortexed thoroughly and incubated for 24 hr at 4-5° C. Following incubation, the solution is centrifuged at 14,000×g for 10 min in the cold. The supernatant, which comprises ADDLs, is transferred to a new tube and stored at 4° C. The amounts used ranged from 100 nM to 1000 nM.

Example 4

ADDLs Localization and Thermal Activation/Degradation

Figure 33:
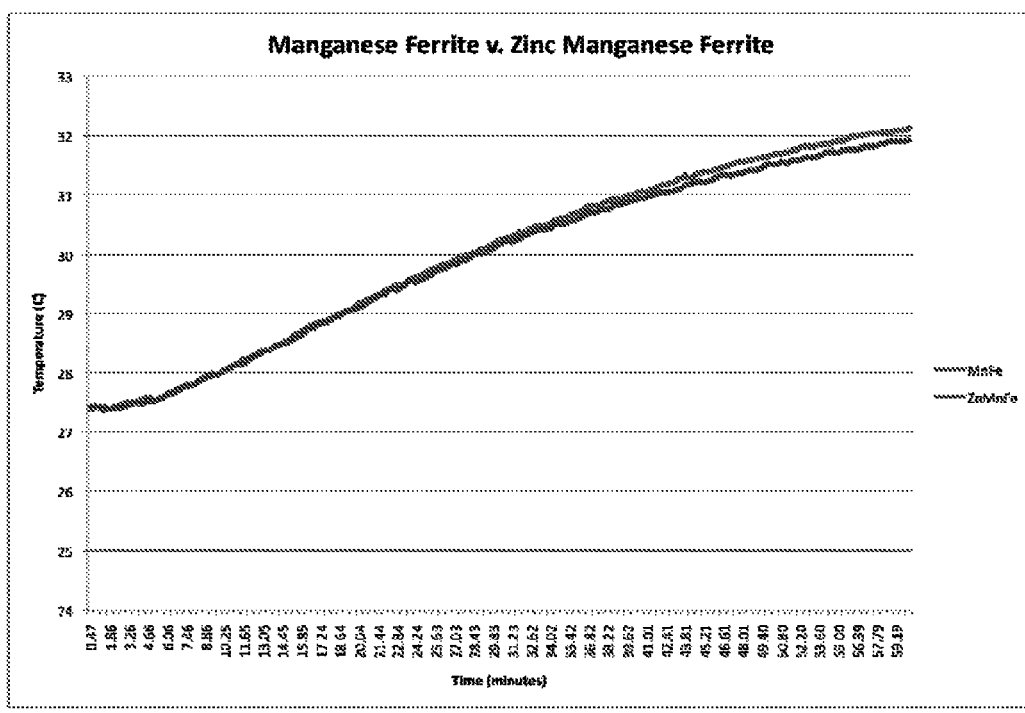
FIG. 33 shows that zinc manganese ferrite nanostructures raised the temperature of solution from room temperature (approximately 27.4° C.) to approximately 32° C.

When placed in a high frequency RF field for one hour, zinc manganese ferrite nanostructures raised the temperature of solution from room temperature (approximately 27.4° C.) to approximately 32° C. The exact temperature curve is shown in FIG. 33. The RF responses of zinc manganese ferrite MNSs and manganese ferrite MNSs of the same size appeared similar.

Previously synthesized ferrite magnetic nanostructures were functionalized with NU-1 antibodies using the crosslinkers SATA and SMCC. The supernatant from this reaction was removed to perform a dot blot in order to determine the binding efficiency of the crosslinker reaction. The functionalized MNSs were then added to different concentrations of ADDLs and allowed to incubate overnight. The supernatant from this reaction was also removed to determine the binding efficiency of the Ab-MNSs. The nanostructures and the ADDLs bound to them were resuspended in phosphate buffered saline and then subjected to a high frequency RF field. After thermal activation, the supernatants were removed and then analyzed using silver stains and western blots to confirm the presence of low molecular weight products. After confirmation, the supernatants were then used to treat neurons in a cell viability study to determine the toxicity of the low molecular weight products.

Figure 34:
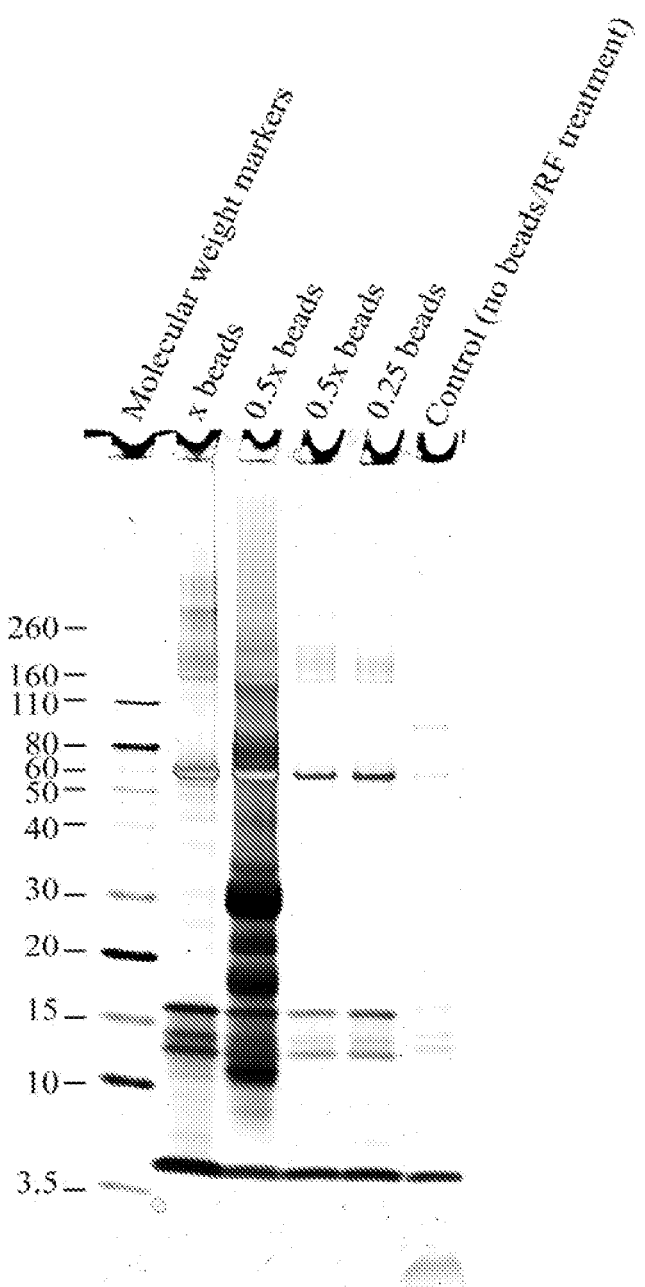
FIG. 34 shows a silver stain of ADDLs after thermal activation by Ab-MNPs.

FIG. 34 shows a silver stain of ADDLs after thermal activation by Ab-MNPs.

Fluorescent Results:

1. 25 ul MNS-NU4/ml 10% NGS with 500 nM FAM ADDLs

Figure 35:
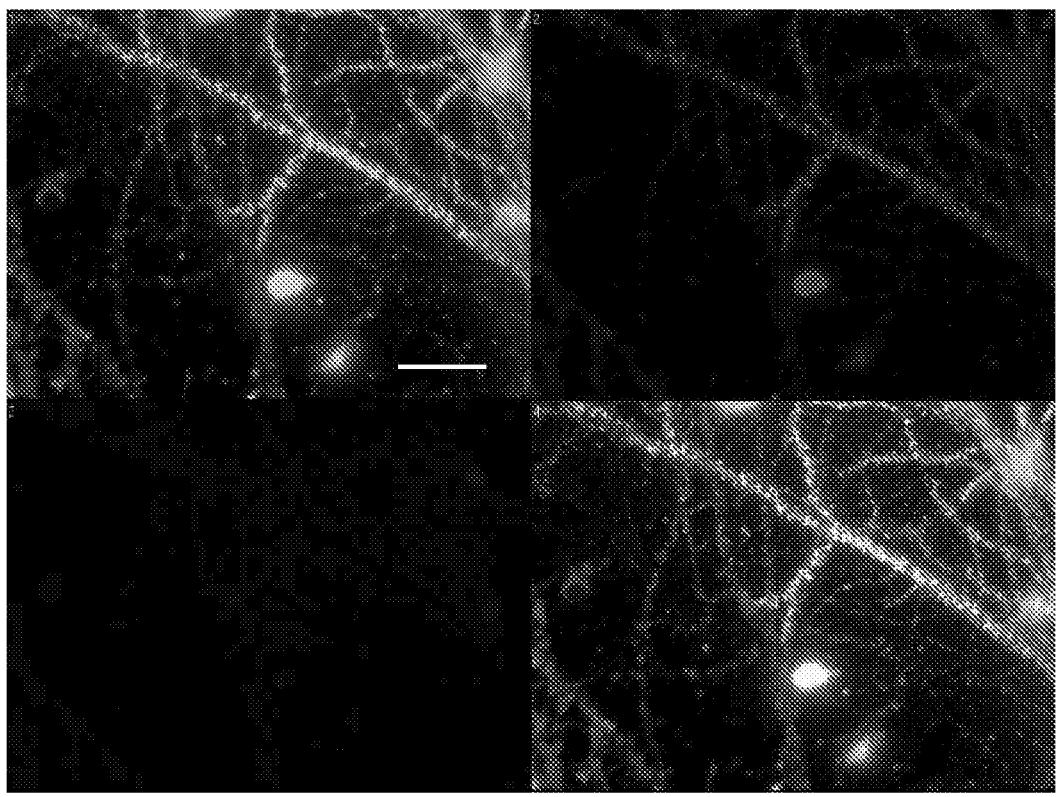
FIG. 35 shows co-localization of fluorescent FAM ADDLs from FITC (top left) and MNS-NU4 (top right) using a Cy5 fluorophore on a goat anti-mouse secondary antibody, which binds the primary NU4 antibody conjugated to the magnetic nanostructures. DAPI (bottom left) stains the nucleus and the merged image displays the 3 channel overlay (bottom right).

FIG. 35 shows co-localization of fluorescent FAM ADDLs from FITC (top left) and MNS-NU4 (top right) using a Cy5 fluorophore on a goat anti-mouse secondary antibody which binds the primary NU4 antibody conjugated to the magnetic nanostructures. DAPI (bottom left) stains the nucleus and the merged image displays the 3 channel overlay (bottom right). Images were taken with an exposure of 15 seconds for FITC and a binning of 2, while the Cy5 channel was taken with an exposure of 10 seconds and binning of 2. The DAPI image exposure was 2.5 seconds with a binning of 2. These are very long exposure times. Scale bar represents 25 um. Images were scaled using MetaMorph Software.

2.25 µl MNS-NU4/ml 10% NGS with (Vehicle/F12) Control

Figure 36:
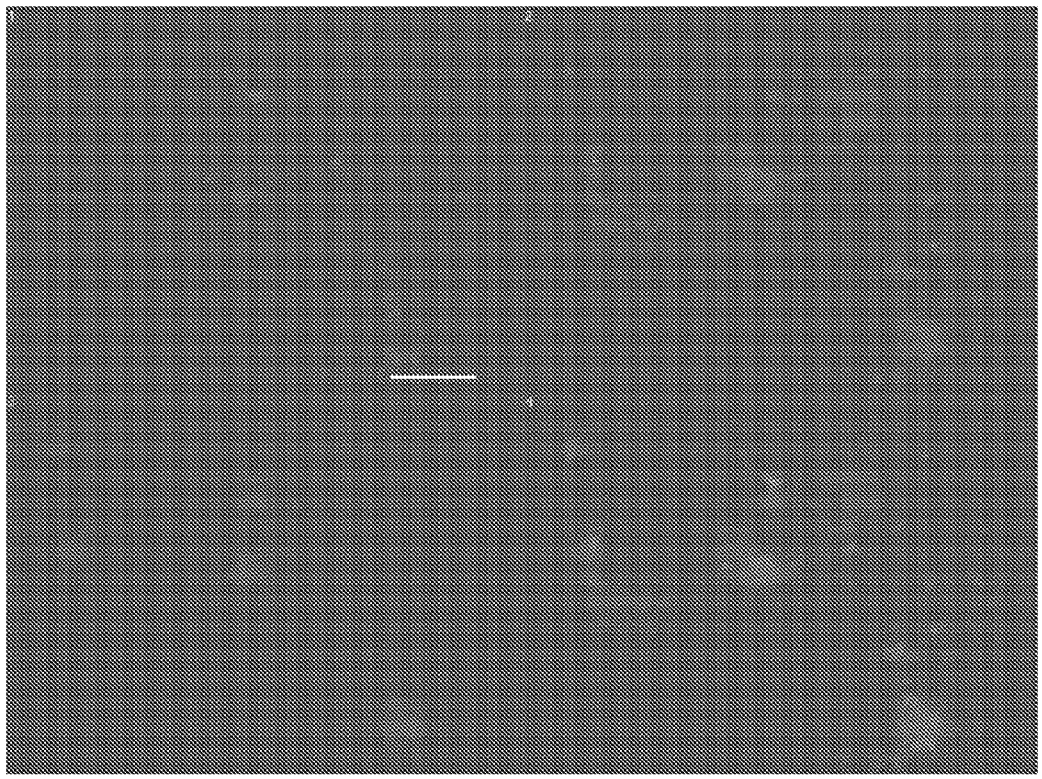
FIG. 36 shows fluorescence in FITC channel (top left) and MNS-NU4 (top right) in Cy5 channel. DAPI (bottom left) stains the nucleus and the merged image displays the 3 channel overlay (bottom right).
Figure 37:
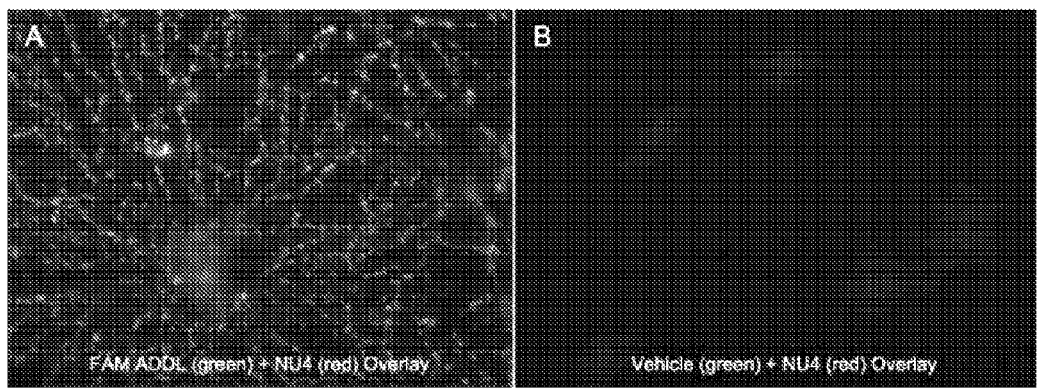
FIG. 37 shows that (A) NU4 antibody, conjugated with AlexaFluor633 dye shows high specificity for fluorescent FAM ADDLs on hippocampal neurons. (B) Clean vehicle control.
Figure 38:
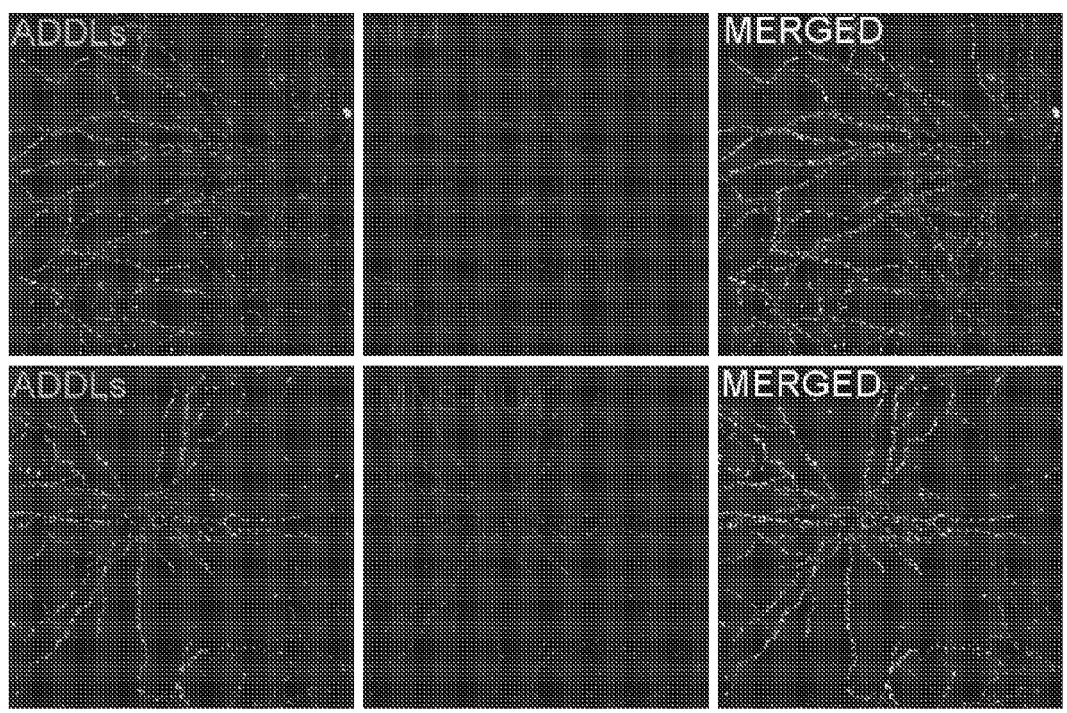
FIG. 38 shows confocal images of neuron culture with FAM ADDLs, AbMNS (NU4 Ab) and merged images; taken with 63× objective on a Leica SP2 confocal microscope.

FIG. 36 shows fluorescence in FITC channel (top left) and MNS-NU4 (top right) in Cy5 channel. DAPI (bottom left) stains the nucleus and the merged image displays the 3 channel overlay (bottom right). Images were taken with an exposure of 15 seconds for FITC and a binning of 2, while the Cy5 channel was taken with an exposure of 10 seconds and binning of 2. The DAPI image exposure was 2.5 seconds with a binning of 2. Scale bar represents 25 um. Images were scaled using MetaMorph Software.

Example 5

ADDLs Specific Antibody Attachment to MNSs (AbMNS) Antibody Preparation, Concentration Determination & Fluorescence Labeling Monoclonal antibodies have been developed that specifically target Amyloid-Beta Derived Diffusible Ligands (ADDLs), the potent oligomeric central nervous system (CNS) neurotoxin attributable to Alzheimer's disease (Lambert et al. Proc. Natl. Acad. Sci. U.S.A 95, 6448-6453 (1998); Lambert et al. J. Neurochem. 79, 595-605 (2001); Lambert et al. Abeta.

J Neurochem. 100, 23-35 (2007). These antibodies, specifically monoclonal NU4, show high specificity for $A\beta_{1-42}$ oligomers compared to monomeric $A\beta_{1-42}$ peptide. ADDLs and fluorescent FAM ADDLs were purchased as monomer and the synthetic ADDL preparation was prepared according to methods described herein. Sodium azide, an antimicrobial storage preservative that interferes with antibody conjugation, was removed from the commercially purchased antibody solution using a 30,000 MW centrifugal NanoSep or Millipore Centricon filter according to manufacturer protocol and two consecutive buffer washes. This control antibody, mouse myeloma IgG1, purchased from Invitrogen, is used as a non-specific antibody control in conjugation to MNS. A far-red fluorescence dye protein labeling kit was purchased from Invitrogen and covalent attachment of 1-3 AlexaFluor633 dye molecules per mole of NU4 antibody or non-specific IgG1 antibody was completed according to the provided protocol. Antibody concentration was determined using UV-vis spectroscopy to measure absorbance at 280 and 632 nm, according to the labeling kit protocol. The provided dye extinction coefficient and an antibody molecular weight of 145 kD was used to calculate the AlexaFluor dye and IgG1 antibody molarity. Antibody was stored without sodium azide until conjugation with MNS. Specificity of dye conjugated NU4 antibody was demonstrated though In Vitro labeling of hippocampal CA1, CA2, CA3 neurons with 100-500 nM FAM ADDLs, followed by treatment with AlexaFluor633 dye conjugated NU4 antibody and fluorescence microscopy.
Determination of MNS Concentration:

Following aqueous phase particle stabilization, the iron concentration of DOPA stabilized MNS was measured against prepared standards after digestion in 3% nitric acid using induced coupled plasma atomic emission spectroscopy (ICP-AES). The MNS particle concentration was estimated by (1) calculating the theoretical number of iron atoms per spherical $Fe_3O_4$ particle based on the average observed TEM diameter (14 or 16 nm) and (2) converting the measured iron concentration to the concentration of $Fe_3O_4$ MNS particles.
Conjugation of MNS with ADDLs-Antibody For conjugation of buffer stabilized MNS with antibodies, the conventional carboxyl-amine conjugation approach based on EDC coupling was used. In this method, the starting material was 250 µL of a 1 mg/mL iron concentration solution of nanostructures. The carboxyl terminated MNS was first activated by adding a 0.1 mol equivalent of sulfo-N-hydroxy succinimide (SNHS) and 0.1 mol equivalent of 1-Ethyl-3-(3-dimethylaminopropyl)carbodiimide (EDC) and allowing the solution to mix on an orbital rotator at 500 rpm for one hour at room temperature. The activated particles were incubated with the corresponding desired antibodies overnight at 4° C. After the conjugation, excess reagent and antibody was separated by a magnet and re-dispersed in working media three times over the course of 3 consecutive days. The first supernatant from these washes was measured using UV-Vis spectroscopy to obtain the absorbance at 280 nm, corresponding to the unbound protein concentration. The amount of conjugated antibodies was determined by subtracting the amount of antibody in the supernatant from the total antibody added. Conjugated particles were stored at 4° C. until use. Conjugated particles were observed to remain in a homogenous solution in PBS (phosphate buffered saline, pH 7.5) for up to 3 hours at room temperature.

An increased concentration of 1-Ethyl-3-(3-dimethylaminopropyl)carbodiimide (EDC) with an accompanying 2 mol EDC equivalent excess of Sulfo-N-Hydroxy succinimide (SNHS) with at least >10 equivalent excess of antibody was used.

Excess antibody was removed using magnetic separation or centrifugation and 2-3 washes with buffer. Antibody concentration in the supernatant was first measured with UV-vis and then a fluorescence standard curve was produced and compared to the fluorescence measured in the supernatant. Initial antibody concentration minus final antibody concentration in the supernatant gives the approximate conjugated antibody.

Example 6

In Vitro Evaluation of AbMNS Targeting ADDLs: IP, Confocal & MR Imaging
In Vitro Hippocampal Neurons & Brain Slice Treatment with AbMNS, Confocal Imaging Cell Culture—Hippocampal cells were prepared and maintained in Neurobasal medium supplemented with B27 (Invitrogen, Carlsbad, Calif.) for at least 2 weeks. Primary CA1, CA2 and CA3 hippocampal neurons plated on coverslips at least 21 DIV were incubated with an equal volume of conditioned media (media the cells had been growing in) containing either 200-500 nM ADDLs (FITC-conjugated ADDL preparation) or vehicle added to each plate/well for 30-45 minutes at 37° C. The cells were incubated at 37° C. The cells were then washed once with 1 mL warm Neurobasal and fixed with 1 mL of 3.7% formaldehyde for 5 minutes. They were then removed and treated a second time with 1 mL of 3.7% formaldehyde for 5 minutes.

ADDL Preparation—ADDLs were prepared according to a published protocol. Briefly, using Aβ peptides (human sequence) that are greater than 95% pure, the $A\beta_{1-42}$ was dissolved in hexafluoro-2-propanol (HFIP) and aliquotted to microcentifuge tubes. Hexafluoro-2-propanol was removed by evaporation with traces removed under vacuum; the tubes are stored at −80° C. An aliquot of $A\beta_{1-42}$ was dissolved in anhydrous dimethyl sulfoxide (DMSO) to 5 mM, which was then added to ice-cold F12 medium without phenol red to 100 µM. This solution was incubated at 4° C. for 24 h and then centrifuged at 14,000 g for 10 min. The supernatant, defined as the ADDL preparation, was transferred to a clean microfuge tube and stored at 4° C. until use. Protein concentration was determined using Coomassie Plus protein assay kit.

Immunohistochemistry—After fixation, the cells were treated with NU4 conjugated magnetic nanostructures (MNS-NU4). A typical concentration of MNS-NU4 used in an ADDLs targeting experiment was 10 µg/ml iron concentration of particles. Treated cells were then imaged under confocal or epi-fluorescence. For confocal analysis of AbMNS/ADDL colocalization, cells were exposed to FAM-ADDLs at 500 nM, a near-saturating dose (assuming 12 Aβ monomer subunits per ADDL) for 1 hour. Scrambled Aβ was used to establish patterns of normal synapse structure and composition. Samples were fixed and then labeled with a quantity of Cy5-AbMNS for 2-3 hours at RT. Samples were mounted and imaged by Confocal fluorescence microscopy (ConFM) of ADDL binding and co-localization. ConFM was used to correlate synaptic binding of FAM-ADDLs (60 minutes) and the localization of the fluorescent Ab-MNS, each measured using immuno-ConFM.
Immunoprecipitation of ADDLs Using AbMNS To demonstrate the specificity of NU4-targeted MNS for ADDLs, immunoprecipitation of ADDLs from solution or human brain extracts and visualizing using a polyclonal anti-ADDL antibody in Western blot was used. It was used to determine that MNS are specifically binding their target as opposed to a non-specific binding by the structures alone.

MNS (NU4 or IgG targeted) were isolated from solution by magnet and resuspended in 1% BSA:F12 with 500 nM ADDLs. MNS and ADDLs were incubated overnight at 4° C. with rotation. MNS were washed with F12 media, then resuspended in Laemmli buffer. MNS were then pelleted with centrifugation/magnet and the supernatant was run on a 4-20% gel, transferred to nitrocellulose, and probed with a polyclonal anti-ADDL antibody.

Figure 39:
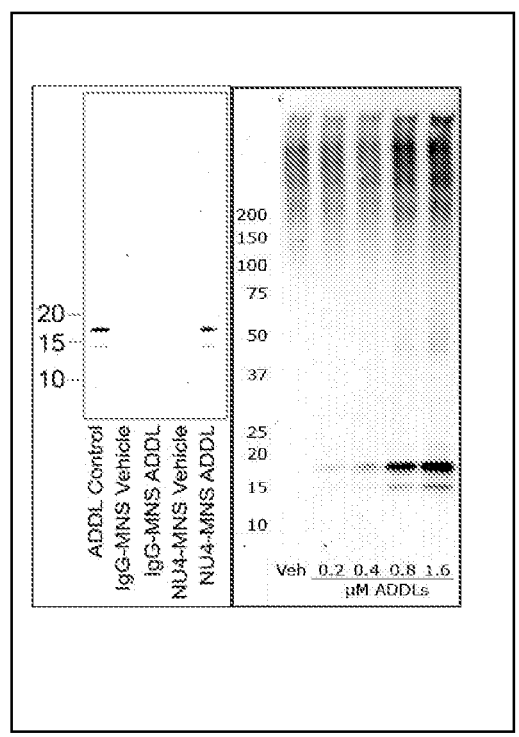
FIG. 39 shows that NU4 conjugated magnetic nanostructures (AbMNS) immunoprecipitate ADDLs from solution with specificity.
Figure 40:
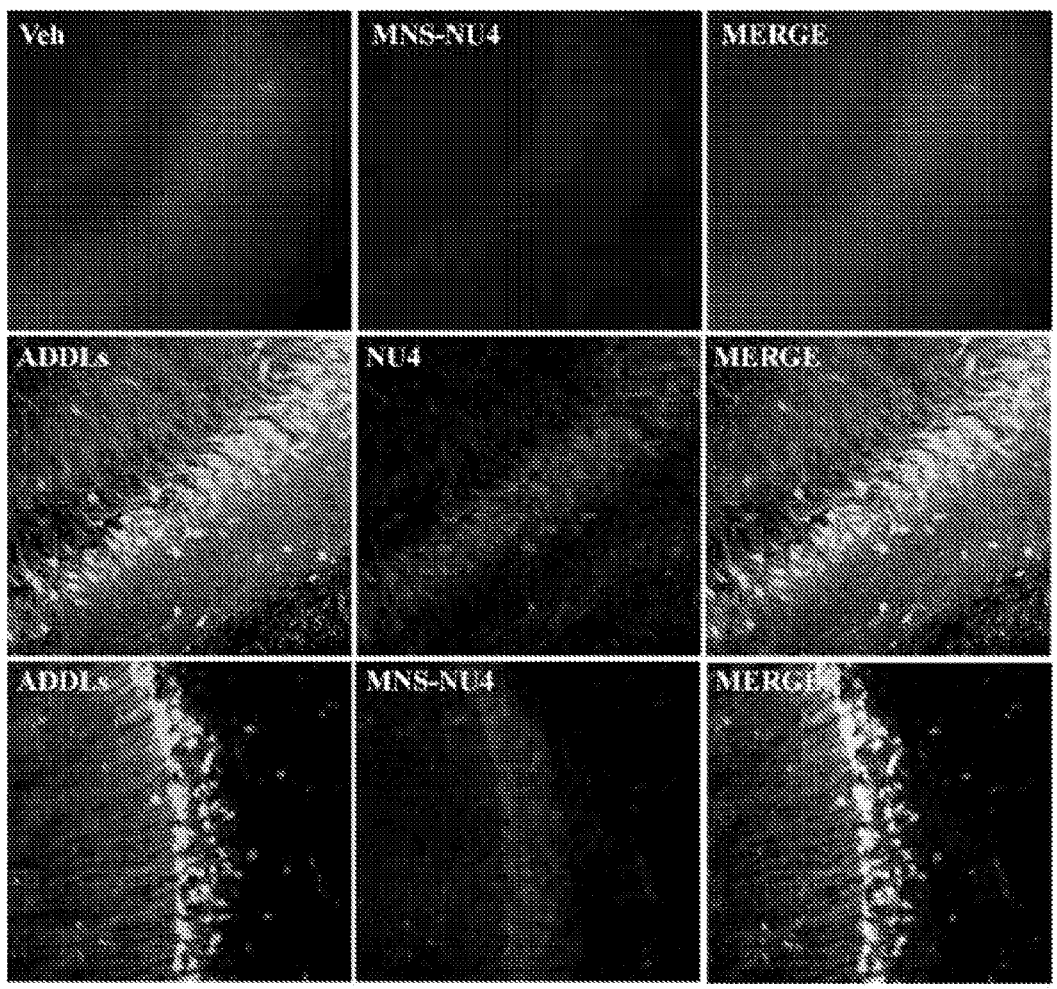
FIG. 40 shows ADDL-dependent MNS-NU4 signal from acute brain slices.

Sodium dodecyl sulfate polyacrylamide gel electrophoresis (SDS-PAGE) was performed according to previously published procedures (Zhang et al. J Biol Chem 269, 25247-25250 (1994)). In brief, samples were added to sample buffer and loaded on a 4-20% Tris-glycine gel. The proteins were separated by electrophoresis at 125 V until the dye front reached the bottom of the gel. Proteins were then transferred to nitrocellulose at 100 V for 1 h in the cold. The membrane was blocked for 1 h at room temperature (23° C.) with 5% non-fat dry milk in Tris-buffered saline (20 mM, pH 7.6, 137 mM NaCl) with 0.1% Tween 20 (TBST). The sample was incubated with primary antibody in blocking buffer for 1.5 h at room temperature and washed 3×15 min. Primary antibody was usually used at a protein concentration of 0.1-0.6 µg/mL, depending on the antibody used. The membrane was incubated with secondary antibody for 1 h at room temperature (1:20,000) and washed the same way. Proteins were visualized with SuperSignal Westo Femto chemiluminescence reagent (Pierce). Quantification utilized Kodak 1D Image Analysis software for the IS440CF Image Station (FIG. 39 Left). Western blot analysis probed with a polyclonal anti-ADDL antibody shows clean IP of 2 ADDL bands with only the NU4-MNS. Bands correspond to those detected in and ADDLs only control lane (FIG. 39. Right). Western blot analysis of increasing concentrations of Aβ oligomers (ADDLs) isolated from solution using Ab-MNS demonstrated that the Ab-MNS bind to and isolate Aβ oligomers proportional to the amount present.

Treatment & Fluorescence Imaging of Animal Hippocampal Brain Slices with AbMNS

Brain Slice Preparation—Artificial cerebro-spinal fluid (ACSF) was prepared and kept at 4° C. according to recipe published by Wang et al. (Brain Res. 924, 133-140 (2002)). The plate on which the slicing was done was kept at 4° C. prior to the preparation. The $O_2$—$CO_2$ bubbler was kept in the ACSF. The brain or the brain slices are not kept in ACSF devoid of $O_2$—$CO_2$ to avoid toxicity to the brain. The brain was removed from the animal's head and placed on a separate plate. The cerebellum was removed and discarded. The hemispheres were separated and one was glued to the chilled plate with Super Glue. The plate and brain were submerged under the chilled ACSF and the bubbler was transferred to the slicing chamber. The brain was sliced into uniformly thick slices of 150-300 µm using a Vibroslice fitted with a new blade. Slices were transferred with a big bore diameter glass pipet to an ACSF-filled chamber with bubbler kept at 37° C. until slicing was complete. Slices were then used for acute assays or grown on membranes for 1-5 days before use as previously published (Lambert et al., 1998, supra; Wang et al., supra), allowing for removal of dead cells and debris that resulted from the slicing insult.

Figure 44:
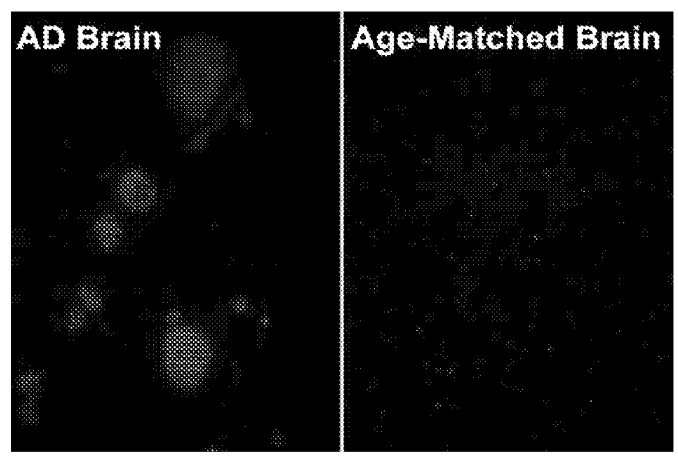
FIG. 44 shows detection of amyloid pathology in AD brain but not age-matched control using fluorescently tagged ADDL-specific antibody, NU4.

Brain Slice Treatment with ADDLs and MNS—Acute hippocampal brain slices were transferred to warm growth media (Neurobasal or Neurobasal A with 1% N-2 supplements) and incubated with varying concentrations of FAM-ADDLs for 1-24 hours. Unbound ADDLs were removed by washing the slices with warm Neurobasal medium 3 times. Slices were fixed with warm 3.7% formaldehyde (50% for 30 minutes followed by 100% for 30 minutes, washed with PBS, and blocked with 10% NGS, and labeled with AbMNS or non-specific IgGMNS (control), FIG. 44. Slices were mounted, placed in a 35 mm dish and covered with sufficient liquid before imaging with the dipping objective on the Leica SP2 confocal microscope.

Magnetic Resonance Imaging of Hippocampal Neurons with AbMNS

Serial Dilutions of MNS—Magnetic Nanostructures (AbMNS) were serially diluted and imaged in a 7T MR scanner, demonstrating decreasing signal intensity.

Figure 45:
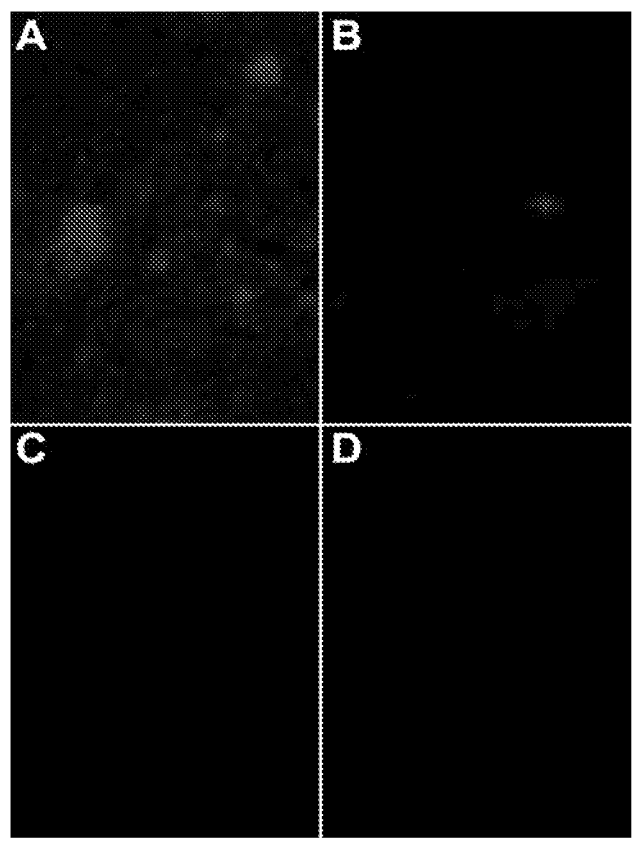
FIG. 45 shows detection of AD pathology in AD brain but not age-matched control using fluorescently tagged NU4-MNS. A) AD brain probed with NU4-MNS; B) Aged control brain probed with NU4-MNS; C) AD brain probed with non-specific IgG-MNS; D) Aged control brain probed with non-specific IgG-MNS.
Figure 46:
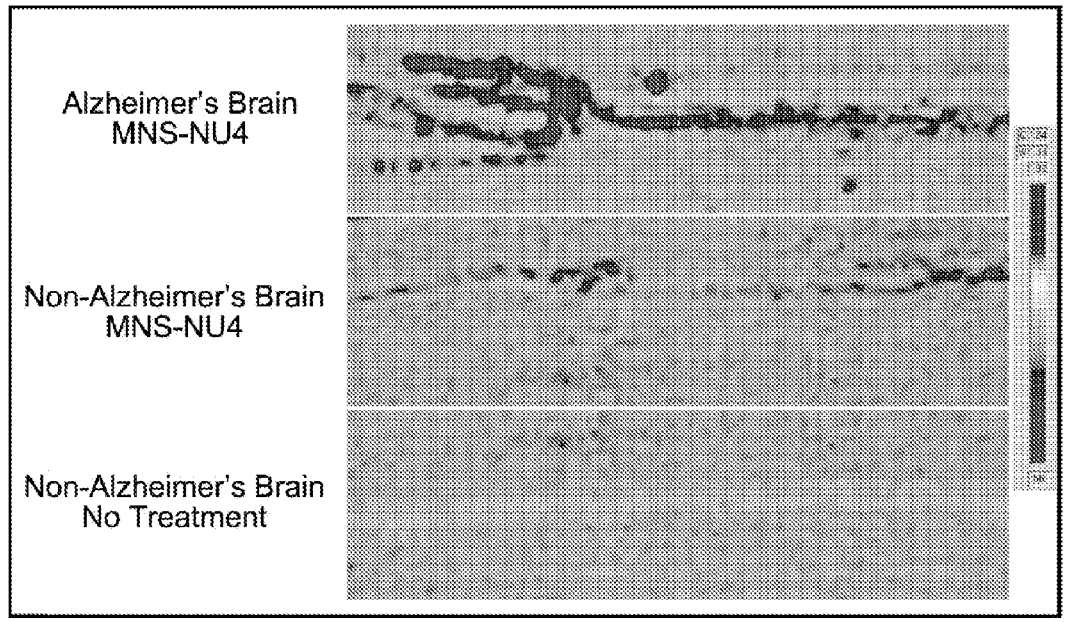
FIG. 46 shows high T2 contrast enhancement of NU4-MNS treated human cortical brain slices in MRI. Image (top) Alzheimer's brain slice treated with NU4-MNS; (middle) Age-matched control brain slice treated with NU4-MNS; (bottom) Age-matched control brain slice with no treatment.

Cell Culture—Hippocampal cells were prepared and maintained as described above. Hippocampal neurons were maintained in Neurobasal medium supplemented with B27 (Invitrogen, Carlsbad, Calif.) for at least 2 weeks as described previously. Cells were incubated in an equal volume of conditioned media (media the cells had been growing in) containing either 500 nM ADDLs (FITC-conjugated ADDL preparation) or vehicle added to each well. The cells were incubated at 37° C., fixed, blocked, and labeled with AbMNS. Cells were then imaged with the Siemens 3T or Bruker 7T MRI scanner (FIGS. 45 and 46).

Treatment & Fluorescence Imaging of Human Cortical Brain Slices with AbMNS

Human Brain Slice Preparation—Human brain slices were provided by the brain bank at Northwestern University/Northwestern Memorial Hospital. After autopsy, brain hemispheres were fixed in 4% parafomaldehyde in PBS. Brains were stored in cryopreservative solution. The brain bank provided 100 µm thick slices from the frontal cortex of patients with confirmed AD and age-matched control in cryopreservative.

Human Brain Slice Treatment with 633-NU4 & Imaging—Slices were transferred to Tris-buffered Saline (TBS) with 0.3% Triton X-100 (TBS-TX), blocked with 10% normal goat serum (NGS) in TBS-TX for 1 hour, and incubated with Alexa Fluor™ 633-NU4 antibody diluted 1:1000 in TBS-TX overnight at 4° C. Slices were rinsed with TBS 5 times for 15 mins each and mounted on slides with ProLong™ antifade reagent for visualization.

Validation of NU4 Detection and Characterization of ADDL Binding Patterns in Human Brain Slices.

Figure 41:
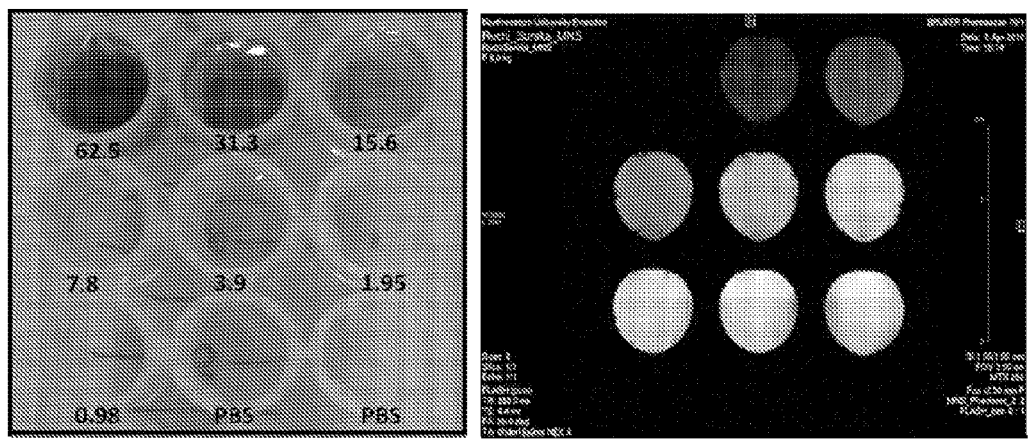
FIG. 41 shows High T2 contrast enhancement of AbMNS suspension in MRI. Photo (left) of serial PBS dilution of AbMNS (µg), and corresponding MRI (right).

The results demonstrate the selectivity of the antibody for Alzheimer's disease (AD) pathology in human brain slices. As seen in FIG. 41, the ADDL-specific antibody used, NU4, selectively binds to plaque and diffuse plaque formations in the AD brain (left) that are not seen in the age-matched control (right). In addition, there are a number of individual neurons that have labeled dendritic arbors. Results demonstrate that the antibody targets AD-related pathology.

Human Brain Slice Treatment with NU4-MNS & Imaging—Slices were transferred to Tris-buffered Saline (TBS) with 0.3% Triton X-100 (TBS-TX), blocked with 10% normal goat serum (NGS) in TBS-TX for 2 days at 4° C., and incubated with 3 mL of diluted Ab-MNS: 0.0075 mg/mL antibody concentration (for comparison, the iron concentration for NU4-MNS: 0.0312 mg/mL Fe and IgG1-MNS: 0.0145 mg/mL Fe) in TBS-TX for 60 hrs at 4° C. Treatment controls were set for similar antibody concentration, compared to similar nanostructure concentration. Slices were rinsed with TBS 5 times for 15 mins each and approximately one-third was mounted on slides with ProLong™ antifade reagent for visualization. A second third of the tissue slice was labeled for iron content using Sigma ACCUSTAIN histological iron stain, which employs the Prussian Blue reaction with free iron. The remaining third was reserved for MRI analysis.

NU4-MNS Detect Similar Structures in Human Brain Slices as Seen with the Cy5-NU4 Antibody.

Figure 42:
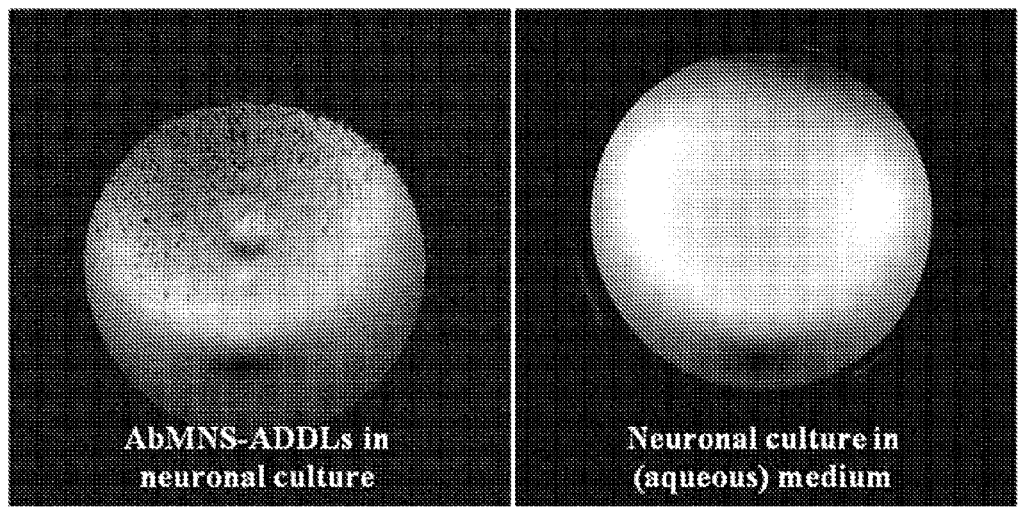
FIG. 42 shows an MRI experiment demonstrating the ability of AbMNS to provide high T2 contrast in MRI.
Figure 43:
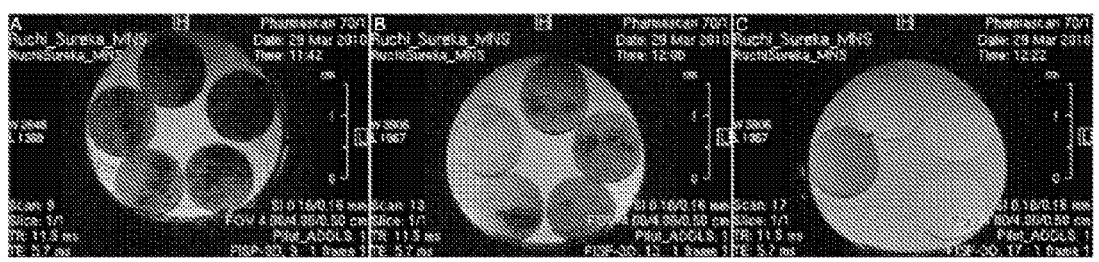
FIG. 43 shows T2 contrast enhancement of AbMNS treated hippocampal neurons on glass coverslips in 35 mm dish. Image A shows high contrast from MNS-NU4 labeling of ADDL treated hippocampal neurons. Image B shows hippocampal neurons without ADDLs treated with AbMNS. Image C shows MR Image of hippocampal neurons with no ADDLs or AbMNS.

The results demonstrated that the conjugation of the ADDL-specific antibody to the magnetic nanostructure did not impair or alter the antibody's ability to target AD pathology in human brains. As seen in FIG. 42, the NU4-MNS probe selectively binds to typical AD pathology, plaques and diffuse plaque formations as well as ADDL-bound dendritic arbors on individual neurons, in the AD brain (A) that are largely absent from the age-matched control (B). Additionally, control treatments consisted of MNS conjugated to non-specific IgG (panels C & D; AD and aged brains, respectively) which showed no non-specific binding. Results not only demonstrate that the conjugation of NU4 to the MNS has no impact on the ability of NU4 to detect AD pathology, but also that the pathology detected was due to recognition by the NU4, not non-specific binding by the MNS.

Magnetic Resonance Imaging of Human Cortical Brain Slices with AbMNS

MR Sample Prep—Human cortical brain slices were treated with AbMNS as described previously. Sample preparation for use with the Bruker 7T animal MR scanner included drilling an opening in a 50 mL conical falcon tube for longitudinal mounting of tissue samples. After storage of treated slices at 4° C., samples were transferred from a suspension in buffer to a layer of low melting point agarose (1%). A second layer of agarose was laid over the tissue slice and a second tissue layer was placed on the agarose. A final layer of agarose was placed on top the second tissue layer. After the agar cooled, the sample was placed in a 7T MRI scanner and imaged. A color table was applied to the original black and white images to highlight differences in T2-weighted contrast.

This result demonstrated high T2-weighted contrast from the use of AbMNS for the imaging of ADDLs using magnetic nanostructures. The age-match controls (non-Alzheimer's brain slices in FIG. 46) show greatly decreased labeling by NU4-MNS, indicating that Ab-MNS functions as an ADDLs-dependent contrast enhanced MR signal agent for Alzheimer's disease.

Example 7

Aqueous Stabilization of MNSs

Figure 47:
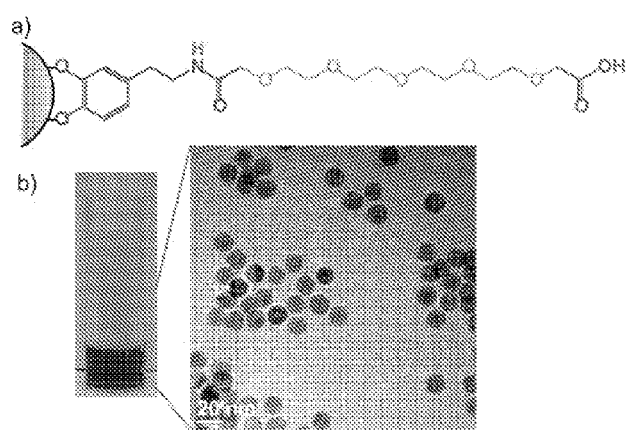
FIG. 47 shows a) Structure of carboxylate terminated ligand stabilized MNS and b) TEM of the aqueous stabilized 20 nm MNS.

Organic phase synthesized MNS were stabilized in aqueous medium. For conjugation with antibody, the MNS were stabilized using carboxylate terminated ligand with dopamine (Xu et al., *J. Am. Chem. Soc.* 2004, 126, 9938-9939) as an anchor (FIG. 47). The stabilization method involved single layer formation of polyethylene glycol ligand on MNS's surface.

Figure 51:
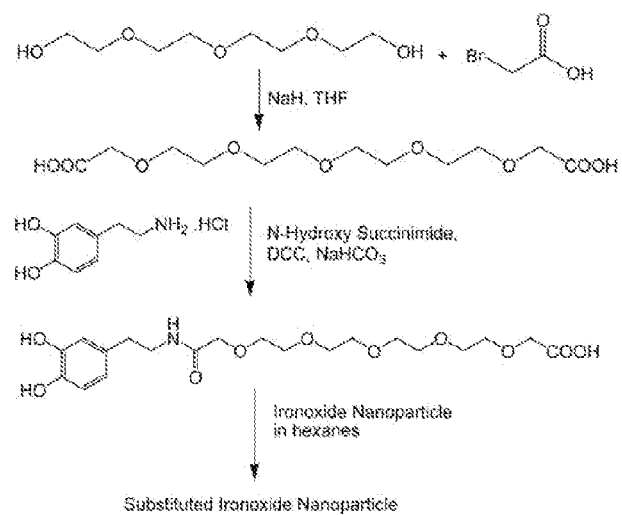
FIG. 51 shows a scheme for synthesis of water/buffer stabilized ironoxide nanoparticle.

Synthesis of carboxylate terminated dopamine ligand and functionalization of MNSs was done according to Scheme 1 shown in FIG. 51. Tetraethyleneglycol diacide, N-hydroxysuccinimide (NHS) (4 mg), N,N'-Dicyclohexylcarbodiimide (DCC) (6 mg), dopamine hydrochloride (4 mg) and anhydrous sodium bicarbonate (6 mg) was dissolved in 3:1 chloroform:DMSO under argon atmosphere and stirred for 4 hours. To this reaction mixture 10 mg hexane stabilized 16 nm ironoxide nanoparticle was added and stirred for another 24 hours for place exchange reaction. It formed a precipitate after 24 hours, which was separated by magnet and dispersed in water by sonication. Aggregates were separated by filtration and filtrate was purified by dialysis.

Figure 48:
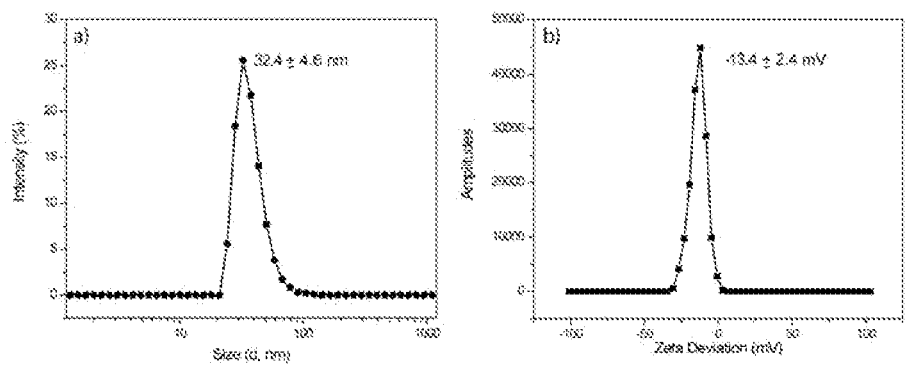
FIG. 48 shows the size (a) and charge (b) of 16 nm iron oxide nanoparticle determined by Malvern zetasizer.

This water dispersible MNS was characterized by TEM, DLS and zeta potential (FIG. 48). TEM showed no aggregation as well as no change in core size. The DLS indicated monodispersity and monolayer formation around MNSs and the negative charge indicated the carboxylate functionality of the MNSs. A similar method was also applied to other shapes and sizes of MNSs.

Figure 49:
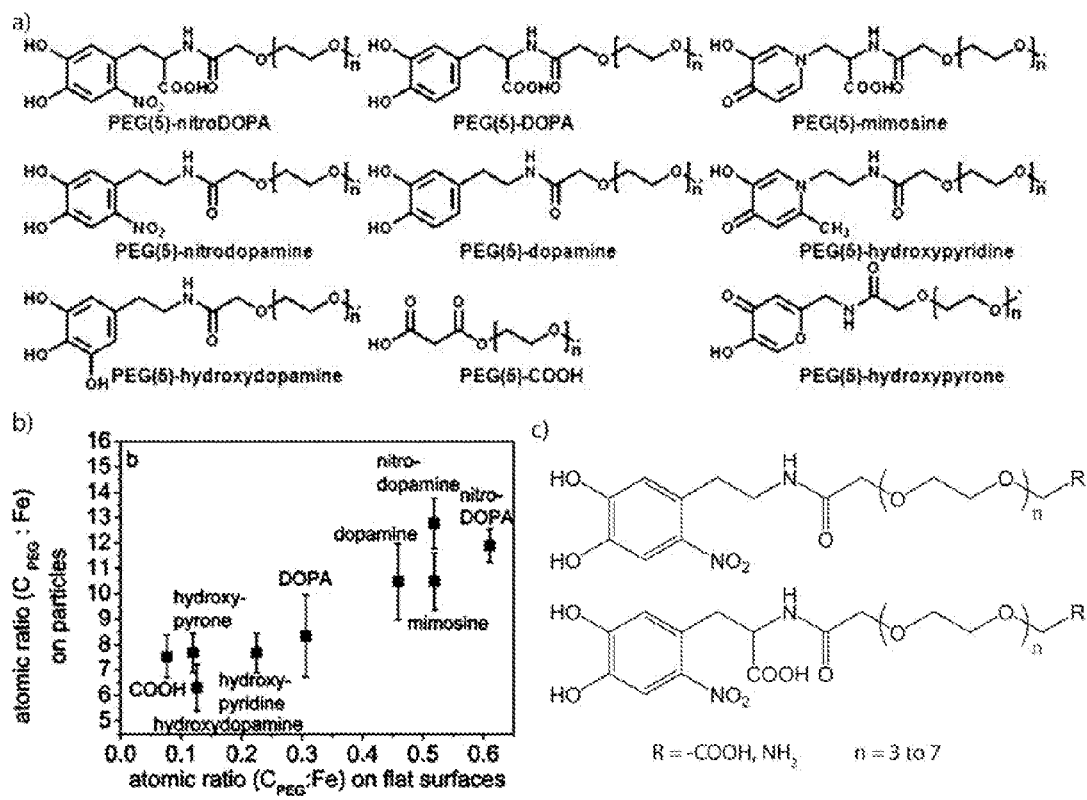
FIG. 49 shows a) Structure of various DOPA, dopamine and their derivative based PEG ligands and b) their relative affinity and stability with iron oxide both on particle and surface determined by XPS studies. c) Nitrodopa ligands for stabilizing MNSs for antibody conjugation.
Figure 50:
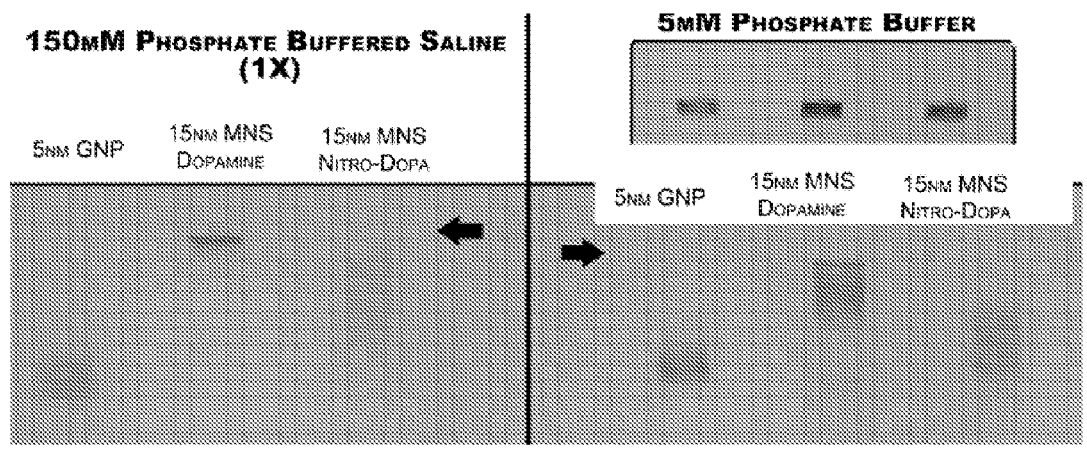
FIG. 50 shows DOPA and Nitro-DOPA stabilized MNSs run in a 1% agarose gel in 150 mM PBS (left) and 5 mM PB (right).

The ferrite MNS stabilization was enhanced using nitrodopamine derivative instead of dopamine. It is known that amino acid DOPA and dopamine possess irreversible binding affinity to iron oxide. Recently it was reported that the nitroderivative of DOPA and dopamine have higher affinity to iron oxide surface which leads to preparation of ultra stable iron oxide nanoparticles under physiologic condition (FIG. 49a,b) (Amstad et al., *Nano Letters* 2009, 9, 4042-4048). Using these DOPA derivatives, a new stabilizing ligand was prepared. The newly stabilized MNSs are very stable in various buffer and media and are suitable for monitoring the conjugation with antibody by gel electrophoresis (FIG. 50). These stabilized MNSs can be produced in bulk quantity.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A system, comprising
   a) a magnetic nanostructure comprising i) a nanoparticle; and ii) a targeting agent, wherein said targeting agent targets said nanostructure to an Aβ-oligomer; and
   b) a device for generating a radio frequency, wherein said magnetic nanostructure generates heat when exposed to a radio frequency generated by said radio frequency generator.

2. The system of claim 1, wherein said targeting agent is an antibody.

3. The system of claim 1, wherein said magnetic nanostructure is coated with a non-magnetic coating.

4. The system of claim 1, wherein said magnetic nanostructure is present in a stable suspension.

5. A method, comprising
   a) administering a magnetic nanostructure comprising i) a nanoparticle; and ii) a targeting agent, wherein said targeting agent targets said nanostructure to an Aβ-oligomer to a subject;
   b) detecting the presence of said Aβ-oligomer in said subject by identifying said magnetic nanostructure; and
   c) destroying said Aβ-oligomer by exposing said magnetic nanostructure to a radio frequency that causes said magnetic nanostructure to generate heat.

6. The method of claim 5, wherein said identifying said magnetic nanostructure comprises the use of magnetic resonance imaging.

7. The method of claim 5, wherein said targeting agent is an antibody.

8. The method of claim 5, wherein said magnetic nanostructure is coated with a non-magnetic coating.

9. The method of claim 5, wherein said magnetic nanostructure is present in a stable suspension.

10. A method, comprising
a) administering a magnetic nanostructure comprising i) a nanoparticle; and ii) a targeting agent, wherein said targeting agent targets said nanostructure to an Aβ-oligomer to a subject; and
b) detecting the presence of said Aβ-oligomer in said subject by identifying said magnetic nanostructure.

11. The method of claim 10, further comprising the step of destroying said Aβ-oligomer by exposing said magnetic nanostructure to a radio frequency that causes said magnetic nanostructure to generate heat.

12. A method, comprising
a) administering a magnetic nanoparticle via injection to the site of an Aβ-oligomer in a subject;
b) detecting the presence of said Aβ-oligomer in said subject by identifying said magnetic nanoparticle; and
c) destroying said Aβ-oligomer by exposing said magnetic nanoparticle to a radio frequency that causes said magnetic nanoparticle to generate heat.

* * * * *

UNITED STATES PATENT AND TRADEMARK OFFICE
CERTIFICATE OF CORRECTION

PATENT NO.        : 9,095,629 B2                                                  Page 1 of 1
APPLICATION NO.   : 13/505167
DATED             : August 4, 2015
INVENTOR(S)       : Dravid et al.

It is certified that error appears in the above-identified patent and that said Letters Patent is hereby corrected as shown below:

Specification

Column 1, lines 12-17 should read:

"STATEMENT REGARDING FEDERALLY SPONSORED RESEARCH OR DEVELOPMENT

This invention was made with government support under U54 CA119341
awarded by the National Institutes of Health, and DMR0603184 awarded by the
National Science Foundation. The government has certain rights in the invention."

Signed and Sealed this
Twelfth Day of January, 2016

Michelle K. Lee
*Director of the United States Patent and Trademark Office*